US008058291B2

(12) United States Patent
Went et al.

(10) Patent No.: US 8,058,291 B2
(45) Date of Patent: Nov. 15, 2011

(54) METHODS AND COMPOSITIONS FOR THE TREATMENT OF CNS-RELATED CONDITIONS

(75) Inventors: Gregory T. Went, Mill Valley, CA (US); Timothy J. Fultz, Pleasant Hill, CA (US)

(73) Assignee: Adamas Pharmaceuticals, Inc., Emeryville, CA (US)

( * ) Notice: Subject to any disclaimer, the term of this patent is extended or adjusted under 35 U.S.C. 154(b) by 1474 days.

(21) Appl. No.: 11/399,879

(22) Filed: Apr. 6, 2006

(65) Prior Publication Data

US 2006/0252788 A1 Nov. 9, 2006

Related U.S. Application Data

(63) Continuation-in-part of application No. 11/285,905, filed on Nov. 22, 2005, now Pat. No. 7,619,007.

(60) Provisional application No. 60/669,290, filed on Apr. 6, 2005.

(51) Int. Cl.
*A01N 43/40* (2006.01)
*A01N 27/00* (2006.01)
*A01N 37/06* (2006.01)
*A61K 31/445* (2006.01)
*A61K 31/015* (2006.01)
*A61K 31/22* (2006.01)
*C07D 401/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)
*C07D 421/00* (2006.01)

(52) U.S. Cl. ......... 514/319; 514/579; 514/766; 546/192
(58) Field of Classification Search .................. 514/319, 514/579, 766; 546/192
See application file for complete search history.

(56) References Cited

U.S. PATENT DOCUMENTS

| | | | |
|---|---|---|---|
| 4,148,896 A | 4/1979 | Smith et al. | |
| 4,273,774 A | 6/1981 | Scherm | |
| 4,346,112 A | 8/1982 | Henkel et al. | |
| 4,767,628 A * | 8/1988 | Hutchinson | 424/426 |
| 4,769,027 A | 9/1988 | Baker et al. | |
| 4,812,481 A | 3/1989 | Reischig et al. | |
| 4,861,800 A | 8/1989 | Buyske | |
| 4,897,471 A | 1/1990 | Tice et al. | |
| 4,904,681 A | 2/1990 | Cordi et al. | |
| 5,057,321 A | 10/1991 | Edgren et al. | |
| 5,061,703 A | 10/1991 | Bormann et al. | |
| 5,061,721 A | 10/1991 | Cordi et al. | |
| 5,086,072 A | 2/1992 | Trullas et al. | |
| 5,162,346 A | 11/1992 | Lobisch et al. | |
| 5,190,763 A | 3/1993 | Edgren et al. | |
| 5,192,550 A | 3/1993 | Edgren et al. | |
| 5,221,536 A | 6/1993 | Edgren et al. | |
| 5,334,618 A | 8/1994 | Lipton | |
| 5,358,721 A | 10/1994 | Guittard et al. | |
| 5,382,601 A * | 1/1995 | Nurnberg et al. | 514/775 |
| 5,395,626 A | 3/1995 | Kotwal et al. | |
| 5,484,608 A | 1/1996 | Rudnic et al. | |
| 5,614,560 A | 3/1997 | Lipton et al. | |
| 5,648,087 A | 7/1997 | Ovaert et al. | |
| 5,891,885 A | 4/1999 | Caruso | |
| 5,912,013 A | 6/1999 | Rudnic et al. | |
| 5,919,826 A | 7/1999 | Caruso | |
| 6,046,232 A | 4/2000 | Kelleher et al. | |
| 6,057,364 A | 5/2000 | Jasys et al. | |
| 6,066,652 A | 5/2000 | Zenner et al. | |
| 6,114,392 A | 9/2000 | Gilad et al. | |
| 6,187,338 B1 | 2/2001 | Caruso et al. | |
| 6,194,000 B1 | 2/2001 | Smith et al. | |
| 6,217,905 B1 | 4/2001 | Edgren et al. | |
| 6,284,276 B1 | 9/2001 | Rudnic et al. | |
| 6,384,083 B1 | 5/2002 | Ludwig et al. | |
| 6,392,104 B1 | 5/2002 | Ishii et al. | |
| 6,444,702 B1 | 9/2002 | Wang et al. | |
| 6,479,553 B1 | 11/2002 | McCarthy | |
| 6,491,949 B2 | 12/2002 | Faour et al. | |
| 6,620,845 B2 | 9/2003 | Wang et al. | |
| 6,717,012 B2 | 4/2004 | Wang et al. | |
| 6,852,889 B2 | 2/2005 | Wang et al. | |
| 7,619,007 B2 | 11/2009 | Went et al. | |
| 2002/0071863 A1 | 6/2002 | Dong et al. | |
| 2003/0203055 A1 | 10/2003 | Rao et al. | |
| 2004/0087658 A1 | 5/2004 | Moebius | |
| 2004/0102525 A1 | 5/2004 | Kozachuk | |
| 2004/0122090 A1 | 6/2004 | Lipton | |
| 2004/0224020 A1 | 11/2004 | Schoenhard | |
| 2005/0031651 A1 | 2/2005 | Gervais et al. | |
| 2005/0065219 A1 | 3/2005 | Lipton et al. | |
| 2005/0124701 A1 | 6/2005 | Went et al. | |
| 2005/0153953 A1 | 7/2005 | Trippodi-Murphy et al. | |
| 2005/0191349 A1 | 9/2005 | Boehm et al. | |
| 2005/0208132 A1 | 9/2005 | Sathyan et al. | |

(Continued)

FOREIGN PATENT DOCUMENTS

AU 2002323873 1/2001

(Continued)

OTHER PUBLICATIONS

2006 Chemical Abstracts Service Catalog. Published 2006 by Chemical Abstracts Service, p. 52.

(Continued)

*Primary Examiner* — Sreeni Padmanabhan
*Assistant Examiner* — Kendra D Carter
(74) *Attorney, Agent, or Firm* — Wilson Sonsini Goodrich & Rosati

(57) ABSTRACT

The present invention provides novel methods and compositions for the treatment and prevention of CNS-related conditions. One of the CNS-related conditions treated by the methods and compositions of the invention is Alzheimer's disease.

58 Claims, 9 Drawing Sheets

U.S. PATENT DOCUMENTS

| | | | |
|---|---|---|---|
| 2005/0209218 A1 | 9/2005 | Meyerson et al. | |
| 2005/0020319 A1 | 10/2005 | Kim et al. | |
| 2005/0245460 A1 | 11/2005 | Meyerson et al. | |
| 2005/0245617 A1 | 11/2005 | Meyerson et al. | |
| 2006/0051416 A1 | 3/2006 | Rastogi et al. | |
| 2006/0052370 A1 | 3/2006 | Meyerson et al. | |
| 2006/0062851 A1 | 3/2006 | Vergez et al. | |
| 2006/0063810 A1 | 3/2006 | Vergez et al. | |
| 2006/0079578 A1* | 4/2006 | Laurin et al. | 514/553 |
| 2006/0142398 A1 | 6/2006 | Went et al. | |
| 2006/0159763 A1 | 7/2006 | Meyer et al. | |
| 2006/0160852 A1 | 7/2006 | Kimura et al. | |
| 2006/0189694 A1 | 8/2006 | Went et al. | |
| 2006/0240043 A1 | 10/2006 | Meyerson et al. | |
| 2006/0246003 A1 | 11/2006 | Kimura et al. | |
| 2007/0065512 A1 | 3/2007 | Dedhiya et al. | |
| 2008/0279819 A1 | 11/2008 | Went et al. | |
| 2010/0047342 A1 | 2/2010 | Went et al. | |
| 2010/0137448 A1 | 6/2010 | Lipton et al. | |

FOREIGN PATENT DOCUMENTS

| | | |
|---|---|---|
| CA | 2323805 A1 | 9/1999 |
| EP | 0392059 A1 | 10/1990 |
| EP | 0451484 A1 | 10/1991 |
| EP | 0488959 A2 | 11/1991 |
| EP | 0488959 A3 | 8/1992 |
| EP | 0502642 A1 | 9/1992 |
| EP | 0870757 A2 | 10/1998 |
| EP | 0927711 A1 | 7/1999 |
| EP | 0870757 A3 | 6/2000 |
| EP | 1509232 | 12/2003 |
| EP | 0452484 B2 | 7/2004 |
| GB | 1173492 A | 12/1969 |
| JP | 58-4718 | 1/1983 |
| JP | 10203966 A | 8/1998 |
| WO | WO 89/09051 A1 | 10/1989 |
| WO | WO 91/06291 A1 | 5/1991 |
| WO | WO 91/14445 A1 | 10/1991 |
| WO | WO 94/05275 A1 | 3/1994 |
| WO | WO 94/06428 A1 | 3/1994 |
| WO | WO 95/13796 A1 | 5/1995 |
| WO | WO 97/14415 A1 | 4/1997 |
| WO | WO 98/18457 A1 | 3/1998 |
| WO | WO 98/27961 A2 | 7/1998 |
| WO | WO 98/27961 A3 | 9/1998 |
| WO | WO 00/18378 A1 | 4/2000 |
| WO | WO 00/56301 A2 | 9/2000 |
| WO | WO 00/56301 A3 | 12/2000 |
| WO | WO 01/19901 A2 | 3/2001 |
| WO | WO 01/32115 A1 | 5/2001 |
| WO | WO 01/32148 A1 | 5/2001 |
| WO | WO 01/46291 A1 | 6/2001 |
| WO | WO 01/62706 A1 | 8/2001 |
| WO | WO 01/19901 A3 | 9/2001 |
| WO | WO 2003/101458 A1 | 12/2003 |
| WO | 2004012700 | 2/2004 |
| WO | WO 2004/012700 A2 | 2/2004 |
| WO | WO 2004/012700 A3 | 4/2004 |
| WO | WO 2004/037234 A2 | 5/2004 |
| WO | WO 2004/056335 A2 | 7/2004 |
| WO | WO 2004/037234 A3 | 8/2004 |
| WO | WO 2004/087116 A2 | 10/2004 |
| WO | WO 2004/056335 A3 | 11/2004 |
| WO | WO 2004/087116 A3 | 12/2004 |
| WO | WO 2004/112768 A1 | 12/2004 |
| WO | 2005065645 | 7/2005 |
| WO | WO 2005/065645 A2 | 7/2005 |
| WO | 2005072705 | 8/2005 |
| WO | WO 2005/072705 A1 | 8/2005 |
| WO | WO 2005/065645 A3 | 10/2005 |
| WO | WO 2005/092009 A2 | 10/2005 |
| WO | WO 2006/009769 A1 | 1/2006 |
| WO | WO 2005/092009 A3 | 2/2006 |
| WO | WO 2006/070781 A1 | 7/2006 |
| WO | WO 2006/089494 A1 | 8/2006 |
| WO | WO 2006/138227 A1 | 12/2006 |

OTHER PUBLICATIONS

Avery's Drug Treatment: Principles and Practice of Clinical Pharmacology and Therapeutics, 3rd Edition, 1987, edited by Trevor M. Speight, Chapter VIII, pp. 255-282.

Bentue-Ferrer, et al. Medication in Alzheimer's disease, Rev. Geriatr. 26(6):511-522 (2001), (in French with English summary).

Braga, et al. Making crystals from crystals: a green route to crystal engineering and polymorphism, Chemical Communications pp. 3635-3645 (2005).

Cacabelos, et al. Pharmacological treatment of Alzheimer disease: From psychotropic drugs and cholinesterase inhibitors to pharmacogenomics, Drugs Today 36(7):415-499 (2000).

Dooley, et al. Donepezil: A review of its use in Alzheimer's Disease, Drugs and Aging 16(3):199-226 (2000).

Feldman, et al. A 24-Week, randomized double-blind study of donepezil in moderate to severe Alzheimer's Disease, Neurology 57:613-20 (2001).

Fuchsberger, et al. Starting Alzheimer therapy in early stages whenever possible. Activities of daily living remain intact longer, MMW Fortschr Med., 144(20):36-9 (2002) (in German with English summary).

Gauthier, et al. Functional, Cognitive, and Behavioral Effects of Donepezil in Patients with Moderate Alzheimer's Disease, Current Medical Research and Opinion® 18(6):347-54 (2002).

Jain, et al. Polymorphism in Pharmacy, Indian Drugs 23(6):315-29 (1986).

Pharmaceutical Dosage Forms: Tablets, Second Edition, Revised and Expanded, published by Marcel Dekker, Inc., edited by Lieberman, Lachman, and Schwartz, pp. 462-472 (1990).

Silverman, R. The Organic Chemistry of Drug Design and Drug Action, published 1992 by Academic Press, pp. 19-21 and 352-401.

The Merck Manual of Diagnosis and Therapy, 17th Edition, published 1999 by Merck Research Laboratories, pp. 1393-1400.

Vippagunta, et al. Crystalline Solids, Advanced Drug Delivery Reviews 48:3-26 (2001).

Yang, et al. Effect of gabapentin derivates on mechanical allodynia-like behaviour in a rat model of chronic sciatic constriction injury, Bioorganic and Medicinal Chemistry Letters 14:2537-41 (2004).

Hartmann S., et al., Tolerability of memantine in combination with cholinesterase inhibitors in dementia therapy, Int. Clin. Psychopharmacol. 2003, 18(2):81-85.

Jain, Evaluation of memantine for neuroprotection in dementia, Exp. Opin. Invest. Drugs 2000, 9(6):1-10.

Periclou A.P., et al., Lack of pharmacokinetic or pharmacodynamic interaction between memantine and donepezil, Ann. Pharmacother. 2004, 38(9):1389-94.

Tariot P.N., et al., Mematine treatment in patients with moderate to severe Alzheimer disease already receiving donepezil: a randomized controlled trial, JAMA 2004, 291(3):317-324.

Wenk, GL., et al., No interaction of memantine with acetylcholinesterase inhibitors approved for clinical use, Life Sci. 2000, 66(12):1079-83.

Hartmann et al., "Tolerability of memantine in combination with cholinesterase inhibitors in dementia therapy", *Int. Clin. Psychopharmacol.*, 18(2):81-85 (2003).

Periclou et al., "Lack of pharmacokinetic or pharmacodynamic interaction between memantine and donepezil", *Ann. Pharmacother.*, 38:1389-1394 (2004).

Tariot et al., "Memantine treatment in patients with moderate to severe Alzheimer disease already receiving donepezil", *JAMA*, 291(3):317-324 (2004).

International Search Report for PCT/US2006/013506, mailed Jan. 12, 2007.

Ambrozi, et al. Treatment of Impaired Cerebral Function in Psychogeriatric Patients with Memantine—Results of a Phase II Double-Blind Study. Pharmacopsychiat. 1988;21(3): 144-6.

Barth, et al. Combination therapy with MK-801 and alpha-phenyl-tert-butyl-nitrone enhances protection against ischemic neuronal damage in organotypic hippocampal slice cultures. Exp Neurol. 1996;141(2):330-6.

Bayerl, et al. Klinsche Vergleichsstudie der Antispastika Memantin and Baclofen. (Clinical Comparative Study of the Antispastic Compounds Memantine and Baclofen). Therapiewozhe 1985;35: 5440-5444. (with English abstract).

Beers, M.H. and Berkow, R. Editors-in-chief, the Merck Manual of Diagnosis and Therapy, 17th Edition, pp. 1525-1544,1999.

Berman, et al. Antidepressant effects of ketamine in depressed patients. Biol. Psychiatry. 2000;47:351-354.

Bhat, et al. Localization of the N-methyl-D-aspartate R1 receptor subunit in specific anterior pituitary hormone cell types of the female rat. Neuroendocrinol. 1995 ;62(2): 178-186.

Bliss, et al. A synaptic model of memory: long-term potentiation in the hippocampus. Nature. 1993;361:31-39.

Bormann, J. Memantine is a potent blocker of N-methyl-D-aspartate (NMDA) receptor channels. Eur. J. Pharmacol. 1989;166:591-592.

Bredt, et al. Localization of nitric oxide synthase indicating a neural role for nitric oxide. Nature. 1990;347:768-770.

Budziszewska, et al. Antidepressant drugs inhibit glucocorticoid receptor-mediated gene transcription—a possible mechanism. Br J Pharmacol. Jul. 2000;130(6):1385-93.

Bull, Drug review—Memantine, Drugs in Context 2005, I(I):1-40.

Calbabrese, et al. A double-blind placebo-controlled study of lamotrigine monotherapy in outpatients with bipolar I depression. Lamictal 602 Study Group. J. Clin. Psychiatry. 1993;60:79-88.

Camps, et al. Cholinergic drugs in pharmacotherapy of Alzheimer's disease. Mini Rev Med Chem. Feb. 2002;2(1):11-25.

Chamulitrat, et al. Nitric oxide formation during light-induced decomposition of phenyl N-tert-butylnitrone. J. Biol. Chem. 1993; 268(16):11520-11527.

Chen, et al. Mechanism of memantine block of NMDA-activated channels in rat retinal ganglion cells: uncompetitive antagonism. J. Physiol. 1997; 499(1):27-46.

Chen, et al. Neuroprotective concentrations of the N-methyl-D-aspartate open-channel blocker memantine are effective without cytoplasmic vacuolation following post-ischemic administration and do not block maze learning or long-term potentiation. Neurosci. 1998;86(4):1121-1132.

Chen, et al. Open-channel block of N-methyl-D-aspartate (NMDA) responses by memantine: therapeutic advantage against NMDA receptor-mediated neurotoxicity. J. Neurosci. 1992;12(11):4427-4436.

Choi, DW. Glutamate neurotoxicity and diseases of the nervous system. Neuron. 1988;1:623-634.

Chung, et al. Clinical pharmacokinetics of doxazosin in a controlled-release gastrointestinal therapeutic system (GITS) formulation, Br J Clin Pharmacol 1999, 48:678-87.

Cohan, et al. Electrically and chemically mediated increases in intracellular calcium in neuronal growth cones. J. Neurosci. 1987;7(11):3588-3599.

Connor, et al. Depolarization- and transmitter-induced changes in intracellular Ca2+ of rat cerebellar granule cells in explant cultures. J. Neurosci. 1987;7(5):1384-1400.

Connor, et al. Sustained dendritic gradients of Ca2+ induced by excitatory amino acids in CA1 hippocampal neurons. Science. 1988;240(4852):649-53.

Cummings, J. L. Depression and Parkinson's Disease: A Review. The American Journal of Psychiatry. 1992;149(4): 443-454.

Cutler, RG. Human longevity and aging: possible role of reactive oxygen species. Ann. New York Acad Sci. 1991;621:1-28.

Danysz, et al. Aminoadamantanes as NMDA receptor antagonists and antiparkinsonian agents—preclinical studies. Neurosci. Biobehav. Rev. 1997;21(4):455-468.

Danysz et al. Memantine provides neuroprotection in animal models at therapeutically relevant doses. Abstracts from the 8th International Conference on Alzheimer's Disease and Related Disorders. Stockholm, Sweden. Jul. 20-25, 2002. No. 297.

Ditzler, K. Efficacy and Tolerability of Memantine in Patients with Dementia Syndrome, Arnzneim.-Forsch./Drug Res. 41 (II), Nr. 8, 773-780 (1991), Bad Krozingen, Germany.

Dreyer, et al. HIV-1 coat protein neurotoxicity prevented by calcium channel antagonists. Science. 1990;248:364-367.

Edamatsu, et al. The spin-trap N-tert-alpha-phenyl-butylnitrone prolongs the life span of the senescence accelerated mouse. Biochem. Biophys. Res. Commun 1995;211(3):847-849.

Edwards, K.R. New Studies on the Pharmacologic Treatment of Painful Neuropathies, Especially in Painful Diabetic Polyneuropathy, 52nd Annual Meeting of the American Academy of Neurology, Apr. 29-May 6, 2000, San Diego, CA, http://www.medscape.com/viewarticle/420246.

Eisenberg, et al. The effects of the clinically tested NMDA receptor antagonist memantine on carrageenan-induced thermal hyperalgesia in rats. Eur. J. Pharmacol. 1994;255(1-3):123-9.

Eisenberg, et al. The NMDA antagonist Memantine blocks pain behavior in a rat model of formalin-induced facial pain. Pain. 1993;54(3):301-7.

European search report dated Oct. 15, 2007 for Application No. 07000173.0.

European Search Report for EP 01 99 0191, mailed May 26, 2004.

FDA Medical Review for Namenda.RTM. NDA 21-487, Oct. 2, 2003, pp. 1-113.

Fischer, et al. The effect of intravenous administration of memantine in parkinsonian patients (author's translation). Arzneimittelforschung. 1977;27(7):1487-1489 (in German with English).

Fleischhacker, et al. Memantine in the treatment of senile dementia of the Alzheimer type. Prog.Prog Neuropsychopharmacol Biol Psychiatry. 1986;10(1):87-93.

Forstl, H. Symptomatic therapy of Alzheimer dementia. Wien Med Wochenschr. 2002;152(3-4):77-80 (in German with English translation).

Foster, et al. Neurobiology. Taking apart NMDA receptors. Nature. 1987;329(6138):395-6.

Fox, et al. Memantine combined with an acetyl cholinesterase inhibitor—hope for the future? Neuropsychiatr Dis Treat. Jun. 2006;2(2):121-5.

Galli, et al. Acetylcholinesterase inhibition and protection by dizocilpine (MK-801) enantiomers. J Pharm Pharmacol. Jan. 1996;48(1):71-6.

Garthwaite, et al. Endothelium-derived relaxing factor release on activation of NMDA receptors suggests role as intercellular messenger in the brain. Nature. 1988;336(6197):385-8.

Gauthier, et al. Effects of memantine on behavioural symptoms in Alzheimer's disease patients: an analysis of the Neuropsychiatric Inventory (NPI) data of two randomised, controlled studies. Int J Geriatr Psychiatry. May 2005;20(5):459-64.

Gelvan, et al. Cardiac reperfusion damage prevented by a nitroxide free radical. Proc. Natl. Acad. Sci. USA. 1991;88(11):4680-4.

Gortelmeyer, et al., Memantine in the Treatment of Mild to Moderate Dementia Syndrome, Arnzneim.-Forsh./ Drug Res. 42 (II), Nr. 7, 904-913 (1992), Frankfurt, Germany.

Graham, et al. Plasma homocysteine as a risk factor for vascular disease. The European Concerted Action Project.JAMA. 1997 277(22):1775-1781.

Greenberg, et al. Treatment of Major Depression and Parkinson's Disease with Combined Phenelzine and Amantadine. Am. J. Psychiatry. 1985;142(2):273-274.

Greene, T.W. Protective Groups in Organic Synthesis. John Wiley & Sons, pp. 70-71 (1981).

Grossmann, et al. Memantine and neurogenic bladder disorders in spastic clinical pictures, Arzneim.-Forsch./Drug Res. 1982, 32(II)(10):1273-6. (in German with English Summary).

Grynkiewicz, et al. A new generation of Ca2+ indicators with greatly improved fluorescence properties. J. Biol. Chem. 1985;260(6):3440-3450.

Gupta, et al. Novel effects of memantine in antagonizing acute aldicarb toxicity: Mechanistic and applied considerations. Drug development research. 1991; 24:329-341.

Gupta, et al. Prevention and antagonism of acute carbofuran intoxication by memantine and atropine. J Toxicol Environ Health. 1989;28(1):111-22.

Hahn, et al. Central mammalian neurons normally resistant to glutamate toxicity are made sensitive by elevated extracellular Ca2+: toxicity is blocked by the N-methyl-D-aspartate antagonist MK-801. Proc. Natl. Acad. Sci. USA. 1998;;85(17):6556-60.

Hartmann, et al. Tolerability of memantine in combination with cholinesterase inhibitors in Alzheimer's disease and vascular dementia. Abstracts from the 8th International Conference on Alzheimer's Disease and Related Disorders. Stockholm, Sweden. Jul. 20-25, 2002. No. 317.

Helmuth, L. New Alzheimer's treatments that may ease the mind. Science. Aug. 23, 2002;297(5585):1260-2.

Ho, et al. Memantine: a New Treatment Option for Patients with Moderate-to-Severe Alzheimer's Disease. P&T, vol. 29 No. 3, Mar. 2004.

Hoffmann, et al. Eight-year prescription trends of memantine and cholinesterase inhibitors among persons 65 years and older in Germany. Int Clin Psychopharmacol. Jan. 2010;25(1):29-36.

Ihl, R. Dementing disorders. What benefits do the new anti-dementia drugs have? MMW Fortschr Med. May 6, 2002;Suppl 2:24-6, 28-9 (in German with English translation).

Jain, K.K. Evaluation of memantine for neuroprotection in dementia. Expert Opin Investig Drugs. Jun. 2000;9(6):1397-406.

Janzen, et al. Stabilities of hydroxyl radical spin adducts of PBN-type spin traps. Free Rad. Biol. Med. 1992;12(2):169-73.

Johnson, et al. Neuropharmacology of phencyclidine: basic mechanisms and therapeutic potential. Annu. Rev. Pharmacol. Toxicol. 1990; 30:707-750.

Karcz-Kubicha, et al. Anxiolytic activity of glycine-B antagonists and partial agonists—no relation to intrinsic activity in the patch clamp. Neuropharmacol. 1997;36(10):1355-67.

Keilhoff, et al. Memantine prevents quinolinic acid-induced hippocampal damage. Eur. J. Pharmacol. 1992;219:451-454.

Klockgether, et al. Excitatory amino acids and the basal ganglia: implications for the therapy of Parkinson's disease. Trends Neurosci. 1989;12(8):285-286.

Klockgether, et al. NMDA antagonists potentiate antiparkinsonian actions of L-dopa in monoamine-depleted rats. Ann Neurol. Oct. 1990;28(4):539-46.

Kornhuber, et al. Amantadine and Memantine are NMDA receptor antagonists with neuroprotective properties. J Neural Transm Suppl. 1994;43:91-104.

Kornhuber, et al. Cerebrospinal fluid and serum concentrations of the N-methyl-D-aspartate (NMDA) receptor antagonist memantine in man. Neurosci. Lett. 1995;195(2):137-9.

Kornhuber, et al. Effects of the 1-amino-adamantanes at the MK-801-binding site of the NMDA-receptor-gated ion channel: a human postmortem brain study. Eur J. Pharmacol. 1991;206(4):297-300.

Kornhuber, et al. Memantine displaces [3H]MK-801 at therapeutic concentrations in postmortem human frontal cortex. Eur. J. Pharmacol. 1989;166(3):589-90.

Kotake, et al. Decay and Fate of the Hydroxyl Radical Adduct of .alpha.-Phenyl-N-tert-butylnitrone in Aqueous Media. J. Am. Chem. Soc. 1991;113:9503-9506.

Krishna, et al. Do nitroxide antioxidants act as scavengers of O2-, or as SOD mimics? J Biol. Chem. 1996;271(42):26026-31.

Krishna, et al. Stimulation by nitroxides of catalase-like activity of hemeproteins. Kinetics and mechanism. J. Biol. Chem. 1996;271(42):26018-26025.

Leskow, P. Therapie zentral bedingter Bewegunggsstorungen: Multicenterstudie mit memantine. Therapiewoche 1987;37:4843-4845.

Letter from British Library dated Aug. 11, 2008 re MMW Fortschritte.

Levy, et al. Comparison of delayed administration of competitive and uncompetitive antagonists in preventing NMDA receptor-mediated neuronal death. Neurol. 1990;40:852-855.

Levy, et al. Redox modulation of NMDA receptor-mediated toxicity in mammalian central neurons. Neurosci. Lett. 1990;110:291-296.

Li, et al. Memantine restores the okadaic acid-induced changes in the activities of protein phosphatase-2a and calcium, calmodulin-protein kinase II and hyperphosphorylation of tau in rat hippocampal slices in culture. Abstracts from the 8th International Conference on Alzheimer's Disease and Related Disorders. Stockholm, Sweden. Jul. 20-25, 2002. No. 421.

Li, et al. Pharmacological reversal of behavioral and cellular indices of cocaine sensitization in the rat. Psychopharmacology (Berl). Aug. 2000;151(2-3):175-83.

Lipton, SA. Prospects for clinically tolerated NMDA antagonists: open-channel blockers and alternative redox states of nitric oxide. Trends Neurosci. 1993;16(12):527-532.

Loveman, et al. Health Technology Assessment. 2006; vol. 10, No. 1 (extract).

Maj, von J. Arzneim-Forsch/Drug Res., 32(10): 1256-1259 (1982) (in German, with Summary in English only).

Masuo, et al. Effects of memantine on the frog neuromuscular junction.Eur. J. Pharmacol. 1986;130(3):187-195.

Mattson, et al. Fibroblast growth factor and glutamate: opposing roles in the generation and degeneration of hippocampal neuroarchitecture. J. Neurosci. 1989;9(11):3728-3740.

Mayer, et al. Excitatory amino acid receptors, second messengers and regulation of intracellular Ca2+ in mammalian neurons. Trends Pharmacol. Sci. 1990;11:254-260.

Mayeux, et al. Treatment of Alzheimer's disease. N. Engl. J. Med. 1999; 341(22):1670-1679.

McCully, K.S. Vascular pathology of homocysteinemia: implications for the pathogenesis of arteriosclerosis. Am. J. Pathol. 1969;56(1):111-128.

McDonald, et al. Physiological and pathophysiological roles of excitatory amino acids during central nervous system development. Brain Res Brain Res Rev. Jan.-Apr. 1990;15(1):41-70.

Mclean, et al. Prophylactic and therapeutic efficacy of memantine against seizures produced by soman in the rat. Toxicol Appl Pharmacol. Jan. 1992;112(1):95-103.

Merello, et al. Effect of memantine (NMDA antagonist) on Parkinson's disease: a double-blind crossover randomized study. Clin. Neuropharmacol. 1999;22(5):273-276.

Miguel-Hidalgo, et al. Memantine prevents β-amyloid -induced neurotoxicity and learning impairment in rats. Abstracts from the 8th International Conference on Alzheimer's Disease and Related Disorders. Stockholm, Sweden. Jul. 20-25, 2002. No. 385.

Miltner, F.O. Utility of symptomatic therapy with memantine in cerebral coma. Arzneimittelforschung, 32(10):1271-1273 (1982) (in German, with English).

Mohsen, et al. Do nitroxides protect cardiomyocytes from hydrogen peroxide or superoxide? Mol. Cell. Biochem.1995;145(2): 103-110.

Montgomery, et al. Profiles of Antidepressant Activity with the Montgomery-Asberg Depression Rating Scale. Acta Psychiatr Scand Suppl. 1985; 320:38-42.

Moryl, et al. Potential antidepressive properties of amantadine, memantine and bifemelane. Pharmacol. Toxicol. 1993;72(6):394-397.

Murray, et al. A facile one-step synthesis of C-arylnitrones using dimethyldioxirane. J. Org. Chem. 1990; 55:2954-2957.

Nikolajsen, et al. Memantine (a N-methyl-D-aspartate receptor antagonist) in the treatment of neuropathic pain after amputation or surgery: a randomized, double-blinded, cross-over study. Anesth. Analg. 2000;91:960-966.

Nilsson, et al. Increased Rick of Developing Parkinson's Disease for Patients with Major Affective Disorder: A Register Study. Acta Psychiatr Scand, 2001; 104:380-386.

Nowak, et al. Alterations in the N-methyl-D-aspartate (NMDA) receptor complex in the frontal cortex of suicide victims. Brain Res. 1995;675:157-164.

Nygard, et al. Plasma homocysteine levels and mortality in patients with coronary artery disease. N. Engl. J. Med. 1997;337(4):230-236.

Opposition by Adamas Pharmaceuticals, Inc. against the grant of European Patent 1509232 B1 in the name of H. Lundbeck A/S dated Aug. 19, 2009.

Orgogozo, et al. Efficacy and Safety of Memantine in Patients with Mild to Moderate Vascular Dementia. A Randomized, Placebo-Controlled Trial (MMM 300), Stroke. 2002; 33(7):1834-9.

Ossowska, et al. The effect of NMDA antagonists on footshock-induced fighting behavior in chronically stressed rats. J. Physiol. Pharmacol. 1997;48(1):127-135.

Pantev, et al. Clinical and Behavioural Evaluation in Long-Term Care Patients with Mild to Moderate Dementia Under Memantine Treatment. Zeitschrift fur Gerontopsychologie and psychiatrie, 6 (1993) Heft 2, S. 103-117.

Parsons, et al. Memantine is a clinically well tolerated N-methyl-D-aspartate (NMDA) receptor antagonist—a review of preclinical data. Neuropharmacology, 38:735-767 (1999).

Paul, et al. Adaptation of the N-methyl-D-aspartate receptor complex following chronic antidepressant treatments. J. Pharmacol. Exp. Ther. 1994;269(1):95-102.

Popik, et al. Chronic treatment with antidepressants affects glycine/NMDA receptor function: behavioral evidence. Neuropharmacol. 2000;39:2278-2287.

Popik, et al. The NMDA antagonist memantine blocks the expression and maintenance of morphine dependence. Pharmacol. Biochem. Behavior 1996;53(4):791-797.

Rabey, et al. Efficacy of Memantine, an NMDA Receptor Antagonist, in the Treatment of Parkinson's Disease. J Neural Transm. 1992; 4:277-82.

Rammes, et al. The N-methyl-D-aspartate receptor channel blockers memantine, MRZ 2/579 and other amino-alkyl-cyclohexanes antagonise 5-HT(3) receptor currents in cultured HEK-293 and N1E-115 cell systems in a non-competitive manner. Neuroscience Letters, 306(1-2):81-84, Jun. 22, 2001.

Rausch, et al. Effects of L-deprenyl and amantadine in an MPTP-model of parkinsonism. J. Neural Transm. 1990;32:269-275.

Reisberg, et al. Long-term treatment with the nmda antagonist memantine: results of a 24-week, open-label extension study in moderately severe-to-severe Alzheimer's disease. Abstracts from the 8th International Conference on Alzheimer's Disease and Related Disorders. Stockholm, Sweden. Jul. 20-25, 2002. No. 2039.

Reisberg, et al. Memantine in moderate-to-severe alzheimer's disease, N. Eng. J. Med. 2003; 348(14):1333-1341.

Reiser, et al. Memantine (1-amino-3,5-dimethyladamantane) blocks the serotonin-induced depolarization response in a neuronal cell line. Brain Res. 1988;443(1-2):338-44.

Riederer, et al. Pharmacotoxic psychosis after memantine in Parkinson's disease. Lancet. 1991;338:1022-1023.

Rieke, et al. Effectiveness and tolerance of memantine in patients with dementia. Die Medizinische Welt, 47:251-254 (1996) (in German with English).

Sack, et al. Antioxidant treatment with phenyl-alpha-tert-butyl nitrone (PBN) improved the cognitive performance and survival of aging rats. Neurosci. Lett. 1996;205(3):181-184.

Samuni, et at. A novel metal-free low molecular weight superoxide dismutase mimic. J. Biol. Chem. 1988;263(34):17921-17924.

Sansom, L.R. Oral extended-release products. Aust Prescr 1999, 22:88-90.

Schmidt, et al. Excitatory amino acids and Parkinson's disease. Trends Neurosci. 1990;13(2):46-47.

Schneider, et al. Effects of oral memantine administration on Parkinson symptoms. Results of a placebo-controlled multicenter study .Dtsch. Med. Wschr. 1984;109(25):987-990. (in German with English abstract).

Schulz, et al. The use of diurnal vigilance changes in the EEG to verify vigilance-enhancing effects of memantine in a clinical pharmacological study. Neuropsychobiol. 1996;33(1):32-40.

Schwab, et al. Amantadine in the treatment of Parkinson's disease. JAMA. May 19, 1969;208(7):1168-70.

Semenova, et al. Low-affinity NMDA receptor channel blockers inhibit acquisition of intravenous morphine self-administration in naive mice. Eur. J. Pharmacol. Jul. 28, 1999;378(1):1-8.

Siemers, E. Recent progress in the treatment of Parkinson's disease. Comprehensive Therapy. 1992; 18(9):20-24.

Skolnick, P. Antidepressants for the new millennium. J. Pharmacol. 1999;375(1-3):31-40.

Smith, et al. Models for studying long-term recovery following forebrain ischemia in the rat. 2. A 2-vessel occlusion model. ACTA Neurol. Scand. 1984;69(6):385-401.

Sviridov, et al. C-hydroxyalkylation of N-adamantylanilines by hexafluoroacetone and methyl trifluoropyruvate. Izv. Akad. Nauk SSSR Ser. Khim. 1989; 10:2348-2350 (English translation).

Tal, M. A novel antioxidant alleviates heat hyperalgesia in rats with an experimental painful peripheral neuropathy. Neuroreport. May 31, 1996;7(8):1382-4.

Third Party Submission in Published Application Under 37 C.F.R.1.99 dated Apr. 20, 2010 regarding U.S. Appl. No. 12/512,701, filed Jul. 30, 2009. 149 pages.

Upchurch, et al. Homocyst(e)ine decreases bioavailable nitric oxide by a mechanism involving glutathione peroxidase.J. Biol. Chem. 1997;272(27):17012-17017.

Walder, et al. Cognitive functioning, cortisol release, and symptom severity in patients with schizophrenia. Biol. Psychiatry. 2000;48(12):1121-1132.

Walsh, et al. Parkinson's Disease and Anxiety. Postgraduate Medical Journal, Feb. 2001; 77:89-93.

Wesemann, et al. Distribution of metabolism of the potential antiparkinson drug memantine in the human. J. Neural Transm. Suppl. 1980;16:143-148.

Wilcock, et al. A Double-Blind, Placebo-Controlled Multicentre Study of Memantine in Mild to Moderate Vascular Dementia (MMM500). Int Clin Psychopharmacol. 2002; 17(6):297-305.

Williams, et al. Calcium gradients in single smooth muscle cells revealed by the digital imaging microscope using Fura-2. Nature. 1985; 318:558-561.

Wilson, et al. Combination drug regimens hold great promise for Alzheimer treatment. Science Blog. Available at http://www.scienceblog.com/community/older/archives/K/5/pub5611.html. Accessed Jan. 29, 2010.

Wimo, et al. Effect of long-term treatment with memantine, and nmda antagonist on costs associated with advanced Alzheimer's disease: results of a 28-week, randomized, double-blind, placebo-controlled study. Abstracts from the 8th International Conference on Alzheimer's Disease and Related Disorders. Stockholm, Sweden. Jul. 20-25, 2002. No. 167.

Wimo, et al. Pharmacoeconomics and dementia. Abstracts from the 8th International Conference on Alzheimer's Disease and Related Disorders. Stockholm, Sweden. Jul. 20-25, 2002. No. 541.

Winblad, et al. Memantine in Severe Dementia: Results of the 9M-Best Study (Benefit and Efficacy in Severly Demented Patients During Treatment with Memantine). Int. J. Geriat. Psychiatry. 1999; 14:135-146. John Wiley & Sons, Ltd.

Yamada, el at. Changes in symptoms and plasma homovanillic acid with amantadine hydrochloride in chronic schizophrenia. Biol Psychiatry. May 15, 1997;41(10):1062-4.

Ziemann, et al. Pharmacological control of facilitatory I-wave interaction in the human motor cortex. A paired transcranial magnetic stimulation study. Electroencephalogr. Clin. Neurophysiol. 1998;109(4):321-330.

Ditzler, K., "Efficacy and Tolerability of Memantine in Patients with Dementia Syndrome," Drug Res. 41 (11), Nr. 8: 773-780 (1991).

Maier et al., "Efficacy of NMDA-receptor antagonist memantine in patients with chronic phantom limb pain—results of a randomized double-blinded, placebo-controlled trial," Pain 103:277-283 (2003).

Swerdlow et al., "The Effects of Memantine on Prepulse Inhibition," Neuropsychopharmacology 34:1854-1864 (2009).

Tariot et al., "Memantine Treatment in Patients With Moderate to Severe Alzheimer Disease Already Receiving Donepezil," JAMA 291(3):317-324 (2004).

* cited by examiner

FIGURE 8

| File name | Description | Tmax | SINGLE DOSE | | dC/dT (*1e5) | % BA |
|---|---|---|---|---|---|---|
| | | | Cmax | AUC | | |
| Namenda | Memantine (5mg) | 6.2 | 0.006 | 629 | 9.63 | 99.2 |
| Namenda | Memantine (20mg) | 6.2 | 0.024 | 2515 | 38.53 | 99.2 |
| Namenda | Memantine (10mg) | 6.2 | 0.012 | 1257 | 19.26 | 99.2 |
| Namenda | Memantine (10mg BID) | 16.8 | 0.023 | 2467 | 13.63 | 99.2 |
| Aricept | Donepezil (10mg) | 5.3 | 0.010 | 1133 | 18.87 | 99.6 |
| | | | | | | |
| NPI-6272 | Memantine Medium (Medium donepezil) | 19.7 | 0.020 | 2291 | 10.25 | 80.0 |
| NPI-6170 | Memantine Fast (IR donepezil) | 13.0 | 0.024 | 2685 | 18.62 | 94.2 |
| NPI-6373 | Memantine Slow (Slow donepezil) | 20.4 | 0.019 | 2126 | 9.79 | 75.0 |
| NPI-6173 | Memantine Fast (Slow donepezil) | 13.6 | 0.024 | 2670 | 17.65 | 94.0 |
| NPI-6370 | Memantine Slow (IR donepezil) | 21.7 | 0.022 | 1992 | 10.48 | 70.0 |
| | | | | | | |
| NPI-6272 | Donepezil Medium (Memantine Medium) | 13.5 | 0.009 | 1061 | 6.89 | 93.4 |
| NPI-6170 | Donepezil IR (Memantine Fast) | 6.1 | 0.010 | 1131 | 16.39 | 99.3 |
| NPI-6373 | Donepezil Slow (Memantine Slow) | 13.6 | 0.009 | 1052 | 7.96 | 92.5 |
| NPI-6173 | Donepezil Slow (Memantine Fast) | 17.0 | 0.008 | 986 | 5.66 | 86.8 |
| NPI-6370 | Donepezil IR (Memantine Slow) | 6.0 | 0.010 | 1129 | 16.67 | 99.0 |

All non_Namenda data was modeled with 22.5mg
Namenda (80%-120%) 2011-3017
BOLD= The dC/dT was adjusted for dissolution lag. (lag value is based on time at Cp=0)
memantine T1/2= 69hr
Donepezil T1/2=75hr

METHODS AND COMPOSITIONS FOR THE TREATMENT OF CNS-RELATED CONDITIONS

RELATED APPLICATION

This application claims priority to U.S. Ser. No. 60/669,290, filed Apr. 6, 2005 and is a continuation-in-part of and claims priority to U.S. Ser. No. 11/285,905, filed Nov. 22, 2005 now U.S. Pat. No. 7,619,007, the contents of which are incorporated herein by reference in their entirety.

FIELD OF THE INVENTION

This invention relates to methods and compositions for treating CNS-related conditions, such as Alzheimer's disease.

BACKGROUND OF THE INVENTION

Acute and chronic neurological and neuropsychiatric diseases are among the leading causes of death, disability, and economic expense in the world. Presently, Alzheimer's disease is the fourth leading cause of death in the USA. Today there is no known cure for this chronic degenerative ailment, which directly affects millions of people throughout the world. Other diseases and disorders of the central nervous system also result in substantial suffering and cost for those afflicted by the ailments as well as their families and providers.

Numerous drugs exist in the market today to treat the symptoms or manage the progression of these diseases, but most have modest or limited efficacy. Frequently, polypharmacy is employed to optimize therapy to the specific needs of patients at different stages of the disease. One of the key challenges in treating these disorders is the high degree of interplay amongst the pathways that control both normal and abnormal neuronal functions. The therapeutic management of these functions is typically determined such that the therapeutic effects are maximized while minimizing the debilitating side effects of the therapies. This effort is usually more complex when multiple therapeutics are employed.

Improved therapeutics for treatment of these diseases and disorders are needed.

SUMMARY OF THE INVENTION

In general, the present invention provides methods and compositions for treating and preventing CNS-related conditions, such as neurodegenerative conditions (e.g., Alzheimer's disease and Parkinson's disease) and pain, by administering to a subject in need thereof a combination that includes an N-Methyl-D-Aspartate receptor (NMDAr) antagonist and a second agent such as acetylcholinesterase inhibitor (AChel). The administration of the combinations described herein results in the alleviation and prevention of symptoms associated with or arising from CNS-related conditions such as Parkinson's disease or Alzheimer's disease including, for example, loss of memory, loss of balance, hallucinations, delusions, agitation, withdrawal, depression, communication problems, cognitive loss, personality change, confusion and insomnia. The combinations of the present invention may be used in the prevention or treatment of CNS-related conditions associated with Alzheimer's disease and may also be helpful for the treatment and prevention of headaches, cerebrovascular diseases, motor neuron diseases, dementias, neurodegenerative diseases, strokes, movement disorders, ataxic syndromes, disorders of the sympathetic nervous system, cranial nerve disorders, myelopathies, traumatic brain and spinal cord injuries, radiation brain injuries, multiple sclerosis, post-meningitis syndrome, prion diseases, myelitic disorders, radiculitis, neuropathies, pain syndromes, axonic brain damage, encephalopathies, chronic fatigue syndrome, psychiatric disorders, glucose dysregulation, and drug dependence.

The NMDAr antagonist, the AChel, or both agents may be administered in an amount similar to that typically administered to subjects. Optionally, the amount of the NMDAr antagonist, the AChel, or both agents may be administered in an amount greater than or less than the amount that is typically administered to subjects. If desired, the amount of the NMDAr antagonist in the pharmaceutical composition is less than the amount of NMDAr antagonist required in a unit dose to obtain the same therapeutic effect for treating or preventing a CNS-related condition when the NMDAr antagonist is administered in the absence of the AChel. Alternatively, the amount of the AChel in the pharmaceutical composition is less than the amount of the AChel required in a unit dose to obtain the same therapeutic effect for treating or preventing a CNS-related condition when the AChel is administered in the absence of the NMDAr antagonist. Optionally, the NMDAr antagonist, the AChel, or both are present at a higher dose than that typically administered to a subject for a specific condition. For example, the amount of memantine (an NMDAr antagonist) required to positively affect the patient response (inclusive of adverse effects) may be 2.5-80 mg per day rather than the typical 10-20 mg per day administered for presently approved indications i.e. without the improved formulations described herein. A higher dose amount of the NMDAr antagonist in the present invention may be employed whereas a lower dose of the NMDAr antagonist may be sufficient when combined with the AChel to achieve a therapeutic effect in the patient. Optionally, lower or reduced amounts of both the NMDAr antagonist and the AChel are used in a unit dose relative to the amount of each agent when administered as a monotherapy. In a preferred embodiment, the amount of the NMDAr antagonist in the pharmaceutical composition is equal to or greater than the amount typically administered to a subject for a specific condition as a monotherapy and the amount of the AChel in the pharmaceutical composition is less than the amount typically administered to a subject for a similar condition.

The invention also provides a pharmaceutical composition that includes an NMDAr antagonist and an AChel. Optionally, a pharmaceutically acceptable carrier is included.

Although compositions comprising a NMDAr antagonist and a second agent such as acetylcholinesterase inhibitor (AChel) have been disclosed (e.g. US 2004/0087658), the problem of providing release of the NMDAr antagonist in a desired manner (e.g. in an amount high enough to treat symptoms or damaging effects of an underlying disease while avoiding undesirable side effects e.g. CNS side effects) when present as a combined therapy has not been addressed. In particular, the presently available dosage forms of NMDAr antagonists need to be administered frequently and require dose escalation at the initiation of therapy to avoid side effects associated with initial exposure to the therapeutic agent. This leads to difficulty in achieving adequate patient compliance, which is further exacerbated by the complicated dosing schedules of therapeutic modalities used for neurological or neuropsychiatric disorders. This problem has not been addressed in the context of providing an NMDAr antagonist as a combined therapy.

Providing a NMDAr antagonist in combination with an AChel requires careful formulation and the pharmacokinetic properties of the two agents will need to be taken into account, for instance to ensure that the amount and rate of release of each of the agents is sufficient for a therapeutic benefit whilst minimizing or avoiding undesired side effects. Further, not only do the pharmacokinetic properties of each of the drugs (e.g. Tmax, drug half-life etc.) need to be considered, but any interaction between the two agents is a further complicating factor.

In one embodiment of the invention, the NMDAr antagonist, the AChel, or both agents may be provided in a controlled or extended release form with or without an immediate release component in order to maximize the therapeutic benefit of each, while reducing unwanted side effects associated with each.

As used herein, "immediate release formulation" refers to a formulation of an active pharmaceutical ingredient that releases greater than 80 percent of the active pharmaceutical ingredient in less than one hour in a USP dissolution method as described herein or by the manufacturer for a commercial product. Typically, the release of the active ingredient in an immediate release formulation is greater than 80 percent in less than 30 minutes as in FIGS. 1A and 2A.

When these drugs are provided in an oral form without the benefit of controlled or extended release components, they are released and transported into the body fluids over a period of minutes to several hours. Thus, the composition of the invention may contain an NMDAr antagonist and a sustained release component, such as a coated sustained release matrix, a sustained release matrix, or a sustained release bead matrix. In one example, memantine (e.g., 5-80 mg) is formulated without an immediate release component using a polymer matrix (e.g., Eudragit), Hydroxypropyl methyl cellulose (HPMC) and a polymer coating (e.g., Eudragit). Such formulations are comprsessed into solid tablets or granules. Optionally, a coating such as Opadry® or Surelease® is used.

As used herein the terms "extended release dosage form", "controlled release dosage form" and "sustained release dosage form" and like expressions are used interchangeably and include dosage forms where the active drug substance or substances are released over an extended period of time. The term "extended" release should be understood in contrast to immediate release and, in particular, the term indicates that the formulation does not release the full dose of the active ingredient immediately after dosing. Such extended release dosage forms typically allow a reduction in dosing frequency as compared to that presented by a conventional dosage form such as a solution or an immediate release dosage form. The extended release forms may or may not comprise an immediate release component.

Optionally, the composition described herein is formulated such that at least one of said NMDAr antagonist or said AChel has an in vitro dissolution profile less than 70% in one hour, less than 90% in two hours, greater than 40% in six hours, and greater than 85% in 12 hours as measured using a USP type 2 (paddle) dissolution system at 50 rpm, at a temperature of 37±0.5° with water as a dissolution medium.

As used herein, "C" refers to the concentration of an active pharmaceutical ingredient in a biological sample, such as a patient sample (e.g. blood, serum, and cerebrospinal fluid). The concentration of the drug in the biological sample may be determined by any standard assay method known in the art. The term "Cmax" refers to the maximum concentration reached by a given dose of drug in a biological sample. The term "Cmean" refers to the average concentration of the drug in the sample over time. Cmax and Cmean may be further defined to refer to specific time periods relative to administration of the drug. The time required to reach the maximal concentration ("Cmax") in a particular patient sample type is referred to as the "Tmax." The agents of the combination are administered in formulations that reduce the variability of the ratio of the concentrations of the active agents over a period of time, thereby maximizing the therapeutic benefit while minimizing the side effects.

In a preferred embodiment, the dosage form is provided in a non-dose escalating, twice per day or once per day form. In such cases, the concentration ramp (or Tmax effect) may be reduced so that the change in concentration as a function of time (dC/dT) is altered to reduce or eliminate the need to dose escalate the drug. A reduction in dC/dT may be accomplished, for example, by increasing the Tmax in a relatively proportional manner. Accordingly, a two-fold increase in the Tmax value may reduce dC/dT by approximately a factor of 2. Thus, the NMDAr antagonist may be provided so that it is released at a rate that is significantly reduced over an immediate release (so called IR) dosage form, with an associated delay in the Tmax. The pharmaceutical composition may be formulated to provide a shift in Tmax by 24 hours, 16 hours, 8 hours, 4 hours, 2 hours, or at least 1 hour. The associated reduction in dC/dT may be by a factor of approximately 0.05, 0.10, 0.25, 0.5, or at least 0.8. In certain embodiments, this is accomplished by releasing less than 30%, 50%, 75%, 90%, or 95% of the NMDAr antagonist into the circulatory or neural system within one hour of such administration.

The provision of such non-dose escalating dosage forms are particularly useful as they provide the drug at a therapeutically effective amount from the onset of therapy further improving patient compliance and adherence and enable the achievement of a therapeutically effective steady-state concentration of the drug in a shorter period of time. This results in an earlier indication of effectiveness and increasing the utility of these therapeutic agents for diseases and conditions where time is of the essence. Furthermore, the compositions of the present invention, by virtue of their design, allow for higher doses of the drug to be safely administered, again increasing the utility of these agents for a variety of indications.

If desired, the NMDAr antagonist or the AChel of the combination is released into a subject sample at a slower rate than observed for an immediate release (IR) formulation of the same quantity of the antagonist. The release rate is measured as the dC/dT over a defined period within the period of 0 to Tmax for the IR formulation and the dC/dT rate is less than about 80% of the rate for the IR formulation. In some embodiments, the dC/dT rate is less than about 60%, 50%, 40%, 30%, 20% or 10% of the rate for the IR formulation. Similarly, the AChel may also be released into a patient sample at a slower rate than observed for an IR formulation of the same quantity wherein the release rate is measured as the dC/dT over a defined period within the period of 0 to Tmax for the IR formulation and the dC/dT rate is less than about 80%, 60%, 50%, 40%, 30%, 20%, or 10%, of the rate for the IR formulation of the same NMDAr antagonist over the first 1, 2, 4, 6, 8, 10, or 12 hours.

Optionally, the sustained release formulations exhibit plasma concentration curves having initial (e.g., from 2 hours after administration to 4 hours after administration) slopes less than 75%, 50%, 40%, 30%, 20% or 10% of those for an IR formulation of the same dosage of the same NMDAr antagonist. The precise slope for a given individual will vary according to the NMDAr antagonist being used, the quantity delivered, or other factors, including, for some active pharmaceutical agents, whether the patient has eaten or not. For other doses, e.g., those mentioned above, the slopes vary directly in relationship to dose.

Using the sustained release formulations described herein, the NMDAr antagonist or the AChEI reaches a therapeutically effective steady state plasma concentration in a subject within the course of the first five, seven, nine, ten, twelve, fifteen, or twenty days of administration. For example, the formulations described herein, when administered at a substantially constant daily dose (e.g., memantine at a dose ranging between 15 mg and 80 mg and preferably between 20 and 45 mg) may reach a steady state plasma concentration in approximately 70%, 60%, 50%, 40%, 30%, or less of the time required to reach such plasma concentration when using a dose escalating regimen.

The ratio of the concentrations of two agents in a combination is referred to as the "Cratio," which may fluctuate as the combination of drugs is released, transported into the circulatory system or CNS, metabolized, and eliminated. An objective of the present invention is to stabilize the Cratio for the combinations described herein. In some embodiments, it is preferred to reduce or even minimize the variation in the Cratio (termed "Cratio,var"). Employing the methods described herein, the release profiles of each active pharmaceutical ingredient may be modified to produce nearly constant Cratios, thereby minimizing Cratio, var. In cases where the Tmax and T1/2 of the NMDAr antagonist and the AChEI are markedly different, e.g. by a factor of two or more, the desired release profiles will likely be dissimilar in order to minimize the relative variability of the active agents between doses.

The present invention therefore features formulations of combinations directed to dose optimization or release modification to reduce adverse effects associated with separate administration of each agent. The combination of the NMDAr antagonist and the AChEI may result in an additive or synergistic response, as described below.

In all foregoing aspects of the invention, at least 50%, 80, 90%, 95%, or essentially all of the NMDAr antagonist in the pharmaceutical composition may be provided in a controlled release dosage form. In some embodiments, at least 99% of the NMDAr antagonist remains in the extended dosage form one hour following introduction of the pharmaceutical composition into a subject. The NMDAr antagonist may have a $C_{max}/C_{mean}$ of approximately 2, 1.6, 1.5, 1.4, 1.3, 1.2 or less, approximately 2 hours to at least 8, 12, 16, 24 hours after the NMDAr antagonist is introduced into a subject. The AChEI may also be provided in a controlled release dosage form. Thus, at least 50%, 60%, 70%, 80%, 90%, 95%, or essentially all of the AChEI may be provided as a controlled release formulation. If provided as such, the AChEI may have a $C_{max}/C_{mean}$ of approximately 2, 1.6, 1.5, 1.4, 1.3, 1.2 or less, approximately 2 hours to at least 6, 8, 12, 16, or 24 hours after the AChEI is introduced into a subject.

The active pharmaceutical agents may be administered to the patient in a manner that reduces the variability of the ratio of the concentrations of the active agents over a period of time, thereby maximizing the therapeutic benefit while minimizing the side effects. The present invention differs from prior studies by providing novel combinations as well as formulations of combinations directed to dose optimization or release modification to reduce adverse effects associated with each agent.

Optionally, the Cratio,var of the NMDAr antagonist and the AChEI is less than 100%, e.g., less than 70%, 50%, 30%, 20%, or 10% after the agents have reached steady-state conditions. Optionally, the Cratio,var of the NMDAr antagonist and the AChEI is less than 100%, e.g. less than 70%, 50%, 30%, 20%, or 10% during the first 24 hours post-administration of the agents. In some embodiments, the Cratio,var is less than about 90% (e.g., less than about 75% or 50%) of that for IR administration of the same active pharmaceutical ingredients over the first 4, 6, 8, or 12 hours after administration.

In all foregoing aspects of the invention, the NMDAr antagonist may be an aminoadamantine derivative including memantine (1-amino-3,5-dimethyladamantane), rimantadine (1-(1-aminoethyl)adamantane), or amantadine (1-amino-adamantane). The AChEI, an acetylcholinesterase inhibitor, may be, e.g., donepezil/ARICEPT®, rivastigmine/EXELON®, galantamine/REMINYL®, tacrine/COGNEX®, metrifonate, or huperzine-A. Thus, in some embodiments, the NMDAr antagonist is memantine while the AChEI is donepezil, rivastigmine, galantamine, tacrine, metrifonate, or huperzine-A.

In some embodiments, the NMDAr antagonist, the AChEI, or both agents are formulated for oral, intravenous, topical, intranasal, subtopical transepithelial, subdermal, or inhalation delivery. Thus, the agents described herein may be formulated as a suspension, capsule, tablet, suppository, lotion, patch, or device (e.g., a subdermally implantable delivery device or an inhalation pump). If desired, the NMDA antagonist and the AChEI may be admixed in a single composition. Alternatively, the two agents are delivered in separate formulations sequentially, or within one hour, two hours, three hours, six hours, 12 hours, or 24 hours of each other. If administered separately, the two agents may be administered by the same or different routes of administration three times a day, twice a day, once a day, or even once every two days. Optionally, the two agents are provided together in the form of a kit. Preferably, the NMDAr antagonist and the AChEI are provided in a unit dosage form.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting. All parts and percentages are by weight unless otherwise specified.

BRIEF DESCRIPTION OF THE FIGURES

FIG. 8 shows pharmacokinetic properties of various IR formulations and SR formulations of the present invention.

DETAILED DESCRIPTION OF THE INVENTION

Figure 1A:
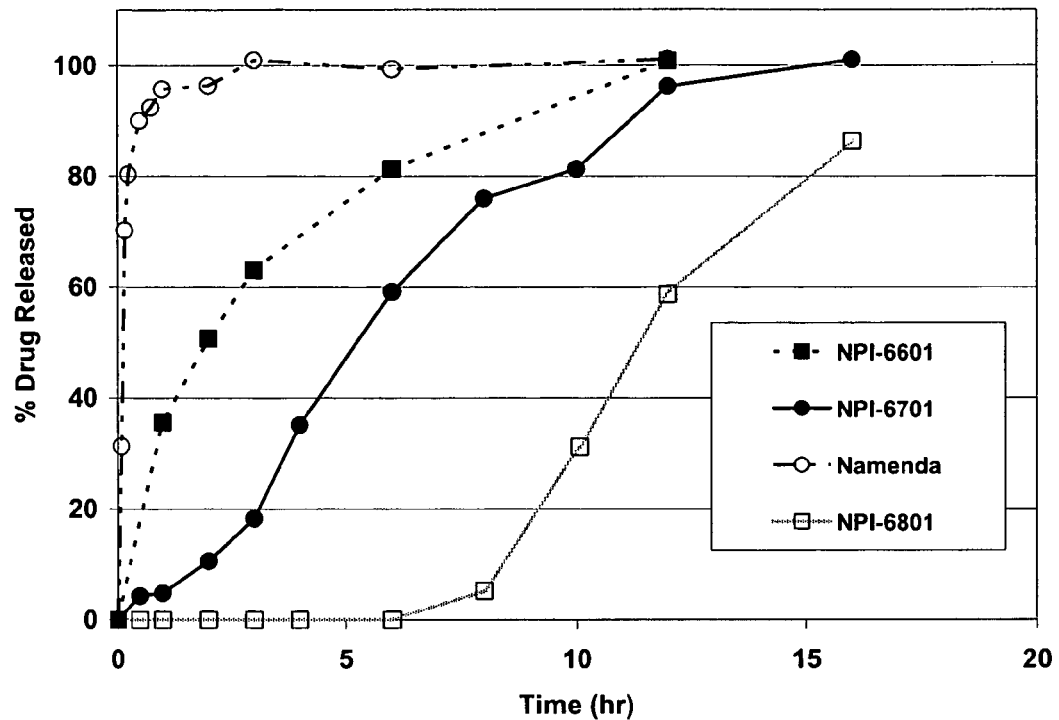
FIG. 1A is a graph showing that the controlled release formulation of memantine (Namenda) and sustained release formulations of memantine (NPI-6601, NPI-6701, and NPI-6801). The sustained release formulations contain 22.5 mg of memantine. These dissolution profiles were obtained from a USP II Paddle system using water as the medium.

The present invention provides methods and compositions for treating or preventing CNS-related conditions, including psychiatric disorders (e.g., panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence (e.g., alcohol, psychostimulants (e.g., crack, cocaine, speed, and meth), opioids, and nicotine), epilepsy, headache, acute pain, chronic pain, neuropathies, cereborischemia, dementias (including Alzheimer's type), movement disorders, and multiple sclerosis. The combination includes a first agent that is an NMDAr antagonist and an AChel (e.g., donepezil/ARICEPT®, rivastignine/EXELON®, galantamine/REMINYL®, tacrine/COGNEX®, metrifonate, or huperzine-A). The combination is administered such that the symptoms associated with CNS-related condition are alleviated or prevented, or alternatively, such that progression of the CNS-related condition is reduced. Desirably, either of these two agents, or even both agents, is formulated for extended release, thereby providing a concentration over a desired time period that is high enough to be therapeutically effective but low enough to reduce or avoid adverse events associated with excessive levels of either agent in the subject. Preferably, the compositions of the present invention are formulated to provide a concentration ratio variability over the dosing interval that is less than that observed or predicted for formulations where neither component or only one component is in an extended release form.

NMDAr Antagonists

Any NMDAr antagonist can be used in the methods and compositions of the invention, particularly those that are non-toxic when used in the combination of the invention. The term "nontoxic" is used in a relative sense and is intended to designate any substance that has been approved by the United States Food and Drug Administration ("FDA") for administration to humans or, in keeping with established regulatory criteria and practice, is susceptible to approval by the FDA or similar regulatory agency for any country for administration to humans or animals.

The NMDAr antagonist may be an amino-adamantane compound including, for example, memantine (1-amino-3,5-dimethyladamantane), rimantadine (1-(1-aminoethyl)adamantane), amantadine (1-amino-adamantane), as well as pharmaceutically acceptable salts thereof. Memantine is described, for example, in U.S. Pat. Nos. 3,391,142; 5,891,885; 5,919,826; and 6,187,338. Amantadine is described, for example, in U.S. Pat. Nos. 3,152,180; 5,891,885; 5,919,826; and 6,187,338. Additional aminoadamantane compounds are described, for example, in U.S. Pat. Nos. 4,346,112; 5,061,703; 5,334,618; 5,382,601; 6,444,702; 6,620,845; and 6,662,845. All of these patents are incorporated herein by reference.

Further NMDAr antagonists that may be employed include, for example, ketamine, eliprodil, ifenprodil, dizocilpine, remacemide, iamotrigine, riluzole, aptiganel, phencyclidine, flupirtine, celfotel, felbamate, neramexane, spermine, spermidine, levemopamil, dextromethorphan ((+)-3-hydroxy-N-methylmorphinan) and its metabolite, dextrorphan ((+)-3-hydroxy-N-methylmorphinan), a pharmaceutically acceptable salt or ester thereof, or a metabolic precursor of any of the foregoing.

The pharmaceutical composition may be formulated to provide memantine in an amount ranging between 1 and 80 mg/day, 5 and 40 mg/day, or 10 and 20 mg/day; amantadine in an amount ranging between 25 and 500 mg/day, 25 and 300 mg/day, or 100 and 300 mg/day; or dextromethorphan in an amount ranging between 1 and 5000 mg/day, 1 and 1000 mg/day, 100 and 800 mg/day, or 200 and 500 mg/day. Pediatric doses will typically be lower than those determined for adults. Representative dosing can be found in the PDR by anyone skilled in the art.

Table 1 shows exemplary the pharmacokinetic properties (e.g., Tmax and T1/2) of memantine, amantadine, and rimantadine.

TABLE 1

Pharmacokinetics and Tox in humans for selected NMDAr antagonists

| Compound | Human PK (t½) in hrs | Tmax in hrs | Normal Dose | Dose Dependent Tox |
|---|---|---|---|---|
| Memantine | 60 | 3 | 10–20 mg/day, starting at 5 mg | Dose escalation required, hallucination |
| Amantadine | 15 | 3 | 100–300 mg/day | Hallucination |
| Rimantadine | 25 | 6 | 100–200 mg/day | Insomnia |

Acetylcholinesterase Inhibitor

The AChel of the combination described herein is an acetylcholinesterase inhibitor (e.g., donepezil/ARICEPT®, rivastigmine/EXELON®, galantamine/REMINYL®, tacrine/COGNEX®, metrifonate, or huperzine-A).

Donepezil, described in U.S. Pat. No. 4,895,841, galantamine, described in U.S. Pat. No. 4,663,318, and rivastigmine, described in U.S. Pat. No. 4,948,807, are all presently approved by the United States FDA for the treatment of mild to moderate Alzheimer's disease. The use of these AChels commonly results in severe nausea, diarrhea, vomiting, and other side effects, including cardiovascular side effects, most of which are dose dependent. Furthermore, the interruption of therapy typically requires re-titration of the dosing starting at the lowest levels (Am. Fam. Phys. 68(7): 136572 (2003)). Ultimately, patients cannot tolerate chronic AChel therapy.

The pharmaceutical composition may be formulated to provide donepezil in an amount ranging between 1 and 10 mg/day, 2 and 5 mg/day, or 2 and 4 mg/day; rivastigmine in an amount ranging between 1 and 12 mg/day, 2 and 6 mg/day, or 2 and 5 mg/day; or galantamine in an amount ranging between 1 and 24 mg/day, 2 and 16 mg/day, or 2 and 12 mg/day. Pediatric doses will typically be lower than those determined for adults. Representative dosing can be found in the PDR by anyone skilled in the art.

Table 2 shows exemplary the pharmacokinetic properties (e.g., Tmax and T1/2) of donepezil, rivastigmine, galantamine, and Huperzine-A.

TABLE 2

Pharmacokinetics and Tox in humans for selected AcheIs

| Compound | Human PK T½ (hrs) | Tmax (hrs) | Normal Dose | Main Dose-Dependent Adverse Event |
|---|---|---|---|---|
| ARICEPT ®/Donepezil | 70 | 3–4 | 5–10 mg/day | Nausea, diarrhea, insomnia |
| EXELON ®/Rivastigmine | 1.5 | 1–2.5 | 6–12 mg/day | Nausea, vomiting |
| REMINYL ®/Galantamine | 7 | 1–2.5 | 16–24 mg/day | Nausea, vomiting, anorexia |
| HUPERZINE-A | 4.8 | 1.3 | 100–400 µg/day | Nausea, hyperactivity, dizziness |

Making Controlled Release Formulations

A pharmaceutical composition according to the invention is prepared by combining a desired NMDAr antagonist or antagonists with one or more additional ingredients that, when administered to a subject, causes the NMDAr antagonist to be released at a targeted concentration range for a specified period of time. The NMDAr antagonist may be provided so that it is released at a dC/dT that is significantly reduced over an instant release (so called IR) dosage form, with an associated delay in the Tmax. The pharmaceutical composition may be formulated to provide a shift in Tmax by 24 hours, 16 hours, 8 hours, 4 hours, 2 hours, or at least 1 hour. The associated reduction in dC/dT may be by a factor of approximately 0.05, 0.10, 0.25, 0.5 or at least 0.8. In addition, the NMDAr antagonist may be provided such that it is released at rate resulting in a $C_{max}/C_{mean}$ of approximately 2 or less for approximately 2 hours to at least 8 hours after the NMDAr antagonist is introduced into a subject.

In addition, the NMDAr antagonist may be provided such that it is released at a rate resulting in a $C_{max}/C_{mean}$ of approximately 2 or less for approximately 2 hours to at least 8 hours after the NMDAr antagonist is introduced into a subject. Optionally, the sustained release formulations exhibit plasma concentration curves having initial (e.g., from 2 hours after administration to 4 hours after administration) slopes less than 75%, 50%, 40%, 30%, 20% or 10% of those for an IR formulation of the same dosage of the same NMDAr antagonist. The precise slope for a given individual will vary according to the NMDAr antagonist being used or other factors, including whether the patient has eaten or not. For other doses, e.g., those mentioned above, the slopes vary directly in relationship to dose. The determination of initial slopes of plasma concentration is described, for example, by U.S. Pat. No. 6,913,768, hereby incorporated by reference.

Optionally, the composition described herein is formulated such the NMDAr antagonist has an in vitro dissolution profile less than 70% in one hour, less than 90% in two hours, greater than 40% in six hours, and greater than 85% in 12 hours as measured using a USP type 2 (paddle) dissolution system at 50 rpm, at a temperature of 37±0.5° with water as a dissolution medium.

Figure 1B:
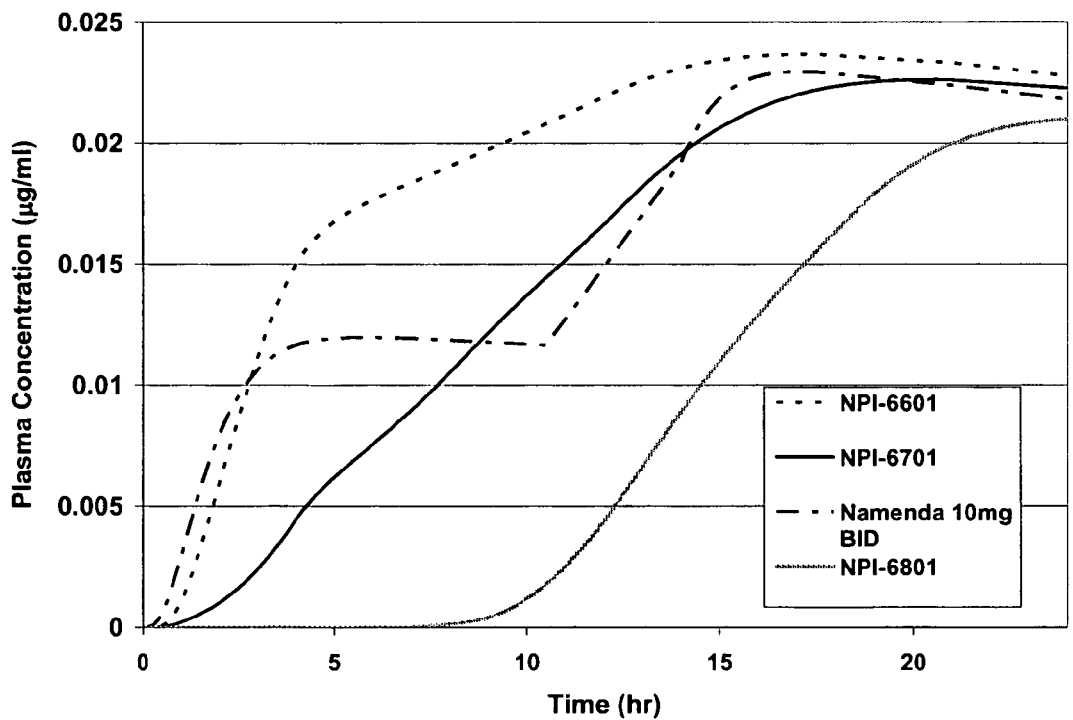
FIG. 1B is a graph showing predicted plasma blood levels for 24 hours of dosing with an immediate release formulation of memantine (Namenda) and sustained release formulations of memantine (NPI-6601, NPI-6701, and NPI-6801), obtained using the Gastro-Plus software package v.4.0.2. The sustained release formulations contain 22.5 mg of memantine.
Figure 2A:
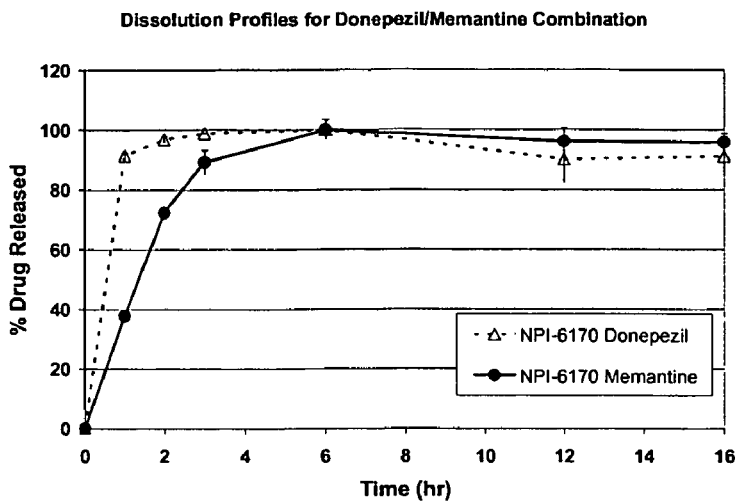
FIG. 2 shows dissolution profile of A) Sustained Release (SR) Memantine (fast)—Immediate Release (IR) Donepezil (NPI-6170), B) SR Memantine (medium)—IR Donepezil (NPI-6270) and C) SR Memantine (slow)—IR Donepezil (NPI-6370).
Figure 2B:
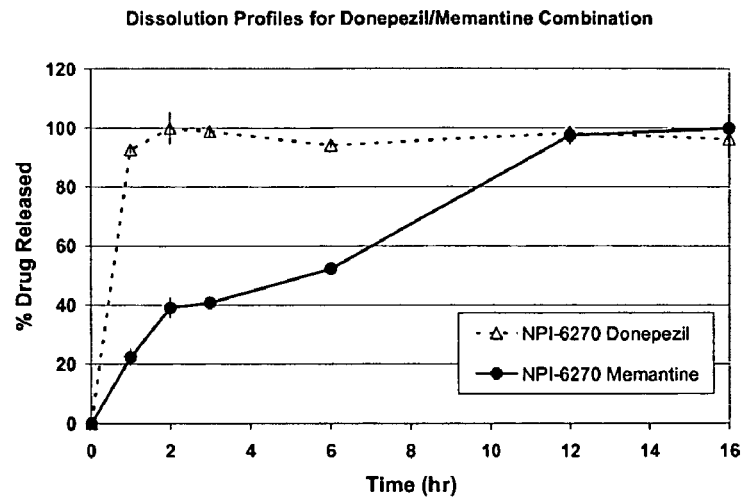
Figure 2C:
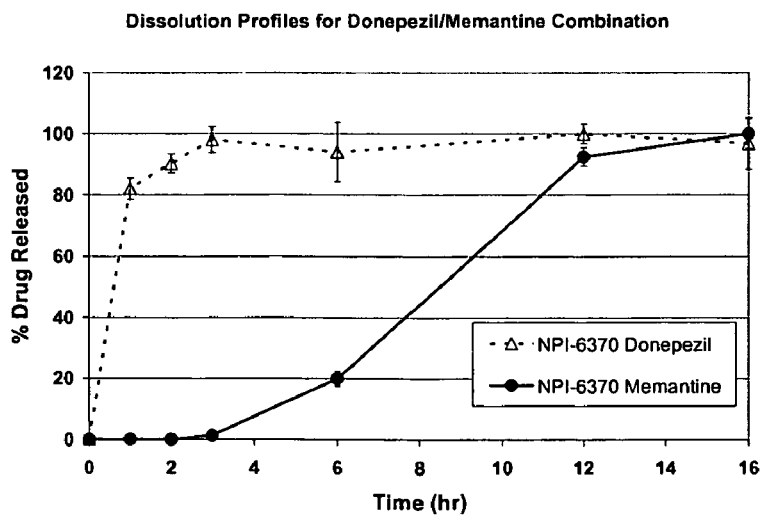
Figure 3A:
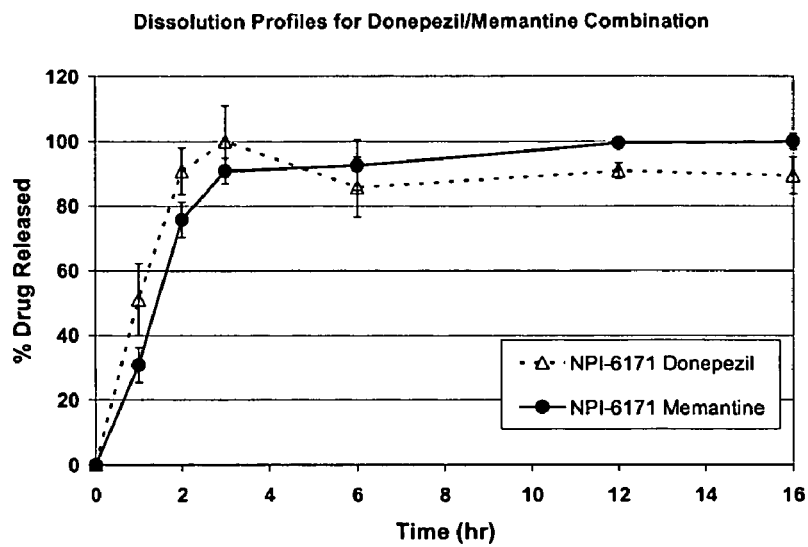
FIG. 3 shows dissolution profile of A) SR Memantine (fast)—SR Donepezil (fast) (NPI-6171), B) SR Memantine (medium)—SR Donepezil (fast) (NPI-6271), C) SR Memantine (slow)—SR Donepezil (fast) (NPI-6371).
Figure 3B:
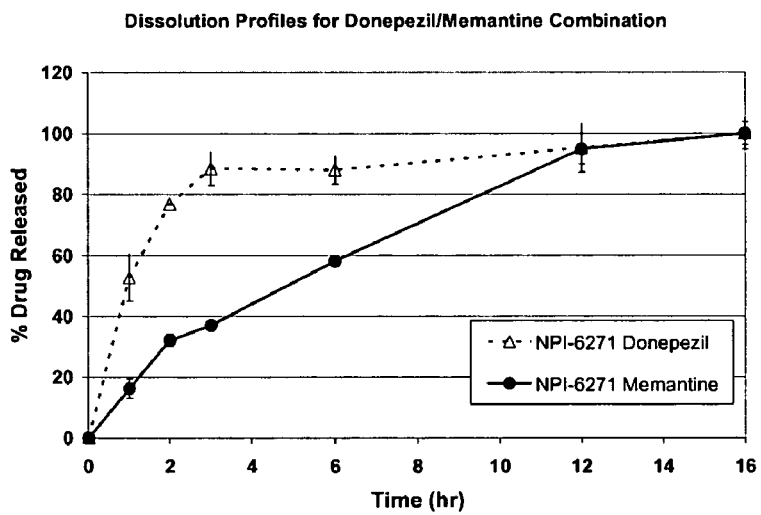
Figure 3C:
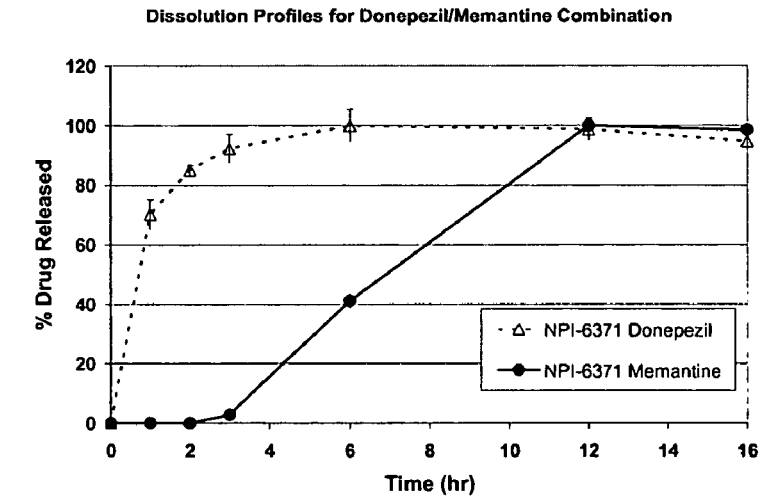
Figure 7:
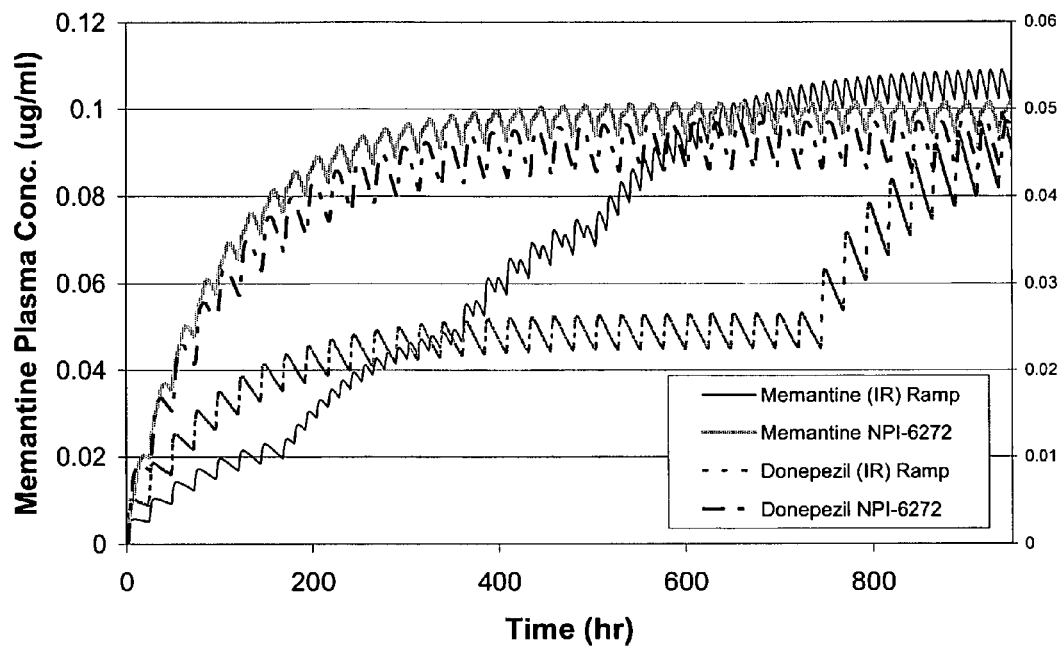
FIG. 7 shows plasma concentrations obtained using the GastroPlus software package v.4.0.2 for an SR Memantine—SR Donepezil forumulation (NPI-6272) and an IR Memantine—IR Donepezil formulation.

Desirably, the compositions described herein have an in vitro dissolution profile that is substantially identical to the dissolution profile shown for the formulations shown in FIGS. 1A and 2-5 and, upon administration to a subject at a substantially constant daily dose, achieves a plasma concentration profile that is substantially identical to those shown in FIGS. 1B, 6, and 7.

A release profile, i.e., the extent of release of the NMDAr antagonist over a desired time, can be conveniently determined for a given time by calculating the $C_{max}/C_{mean}$ for a desired time range. For example, the NMDAr antagonist can be provided so that it is released at $C_{max}/C_{mean}$ of approximately 2 or less for approximately 2 hours to at least 6 hours after the NMDAr antagonist is introduced into a subject. One of ordinary skill in the art can prepare combinations with a desired release profile using the NMDAr antagonists and formulation methods described below.

Optionally, the AChel may also be prepared as a controlled release formulation as described above for the NMDAr antagonist.

Using the formulations described herein, therapeutic levels may be achieved while minimizing debilitating side-effects that are usually associated with immediate release formulations. Furthermore, as a result of the reduction in the time to obtain peak plasma level and the potentially extended period of time at the therapeutically effective plasma level, the dosage frequency may be reduced to, for example, once or twice daily dosage, thereby improving patient compliance and adherence. For example, side effects including psychosis and cognitive deficits associated with the administration of NMDAr antagonists may be lessened in severity and frequency through the use of controlled-release methods that shift the Tmax to longer times, thereby reducing the dC/dT of the drug. Reducing the dC/dT of the drug not only increases Tmax, but also reduces the drug concentration at Tmax and reduces the Cmax/Cmean ratio providing a more constant amount of drug to the subject being treated over a given period of time and reducing adverse events associated with dosing. With regards to the AChel, the lower dC/dT and Cmean will result in a lower incidence of cardiovascular or gastric side effects and other adverse events.

In addition to the specific combinations disclosed herein, combinations made of a first NMDAr antagonist and the AChel may be identified by testing the ability of a test combination of a selected NMDAr antagonist and one or more AChels to lessen the symptoms of a CNS-related disorder. Preferred combinations are those in which a lower therapeutically effective amount of the NMDAr antagonist and/or the AChel is present relative to the same amount of the NMDAr antagonist and/or the AChel required to obtain the same effect when each agent is tested separately.

The amounts and ratios of the NMDAr antagonist and the AChEI are conveniently varied to maximize the therapeutic benefit and minimize the toxic or safety concerns. The NMDAr antagonist may range between 20% and 200% of its normal effective dose and the AChEI may range between 20% to 200% of its normal effective dose. The precise ratio may vary according to the condition being treated. In one example, the amount of memantine ranges between 2.5 and 80 mg per day and the amount of donepezil ranges between 1 and 20 mg/day.

A composition containing a sustained release formulation of memantine may be administered twice a day, once a day, once every two days, or once every three days in a unit dose containing 10-300 mg, 10-200 mg, 10-100 mg, or 10-50 mg of memantine (e.g., 10 mg, 11.25 mg, 12.5 mg, 15 mg, 20 mg, 22.5 mg, 25 mg, 30 mg, 33.75 mg, 37.5 mg, 40 mg, 45 mg, 50 mg, 60 mg, 65 mg, 67.5 mg, 70 mg, 75 mg, 80 mg, 120 mg, 180 mg, 240 mg or 300 mg). When the memantine is in a controlled-release form, the preferred dosage range is 10 mg to 80 mg per day; daily doses of about 22.5, 27.5, 32.5, 37.5, 42.5, 47.5, 52.5, 57.5, 62.5, 67.5, 72.5, 77.5 mg are particularly preferred. When the donepezil is in a controlled-release form, the preferred dosage range 1 mg to 10 mg per day; daily doses of about 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0 mg per day are particularly preferred. In a particularly preferred embodiment the memantine dose is 30-45 mg per day, taken in combination with a donepezil dose of 2-4 mg/day, administered as a single dosage form, with no dose escalation over time. The combination dosage form preferably has sustained release formulations for memantine, donepezil or both, such that the dissolution profile of the two drugs in the combination tablet are "matched", especially with regards to the Tmax, dC/dT (normalized for the dose of NMDAr antagonist and AChEI) in a human. For memantine and donepezil, which have similar pharmacokinetic properties, in vitro dissolution profiles will also be similar.

In a preferred embodiment of this invention, memantine and donepezil are formulated into beads or pellets (as described herein) with substantially similar dissolution profiles. More preferably, beads or pellets of memantine are prepared with a dissolution profiles similar to that shown for memantine in FIG. 4B and, separately, beads or pellets of donepezil are prepared with a dissolution profile similar to that shown for donepezil in the same figure. The preferred pellets are approximately 0.4 mg each and contain approximately 60 μg memantine or donepezil and easily characterized by known methods. The beads may be filled into gelatin capsules by mass or number to achieve the preferred mass of memantine of 30-45 mg per capsules and donepezil of 2-4 mg per capsule. For example, a 42 mg memantine 3.6 mg donepezil combination may be prepared by combining 700 memantine beads with 60 donepezil beads in each capsule, equivalent to 280 mg memantine beads plus 24 mg donepezil beads per capsule.

Additionally, different release profiles for each active pharmaceutical ingredient may be prepared and combined in prescribed ratios to adjust the release profile for each of the ingredients, enabling the more rapid development of formulations for development purposes or specialized formulations for individual products.

For a specified range a physician or other appropriate health professional will typically determine the best dosage for a given patient, according to his sex, age, weight, pathological state, and other parameters. In some cases, it may be necessary to use dosage outside of the range stated in pharmaceutical packaging insert to treat a subject. Those cases will be apparent to the prescribing physician or veterinarian.

In some embodiments, the combinations of the invention achieve therapeutic levels while minimizing debilitating side-effects that are usually associated with immediate release formulations. Furthermore, as a result of the delay in the time to obtain peak plasma level and the potentially extended period of time at the therapeutically effective plasma level, the dosage frequency may be reduced to, for example, once or twice daily dosage, thereby improving patient compliance and adherence.

Accordingly, the combination of the invention allows the NMDAr antagonist and the AChEI to be administered in a combination that improves efficacy and avoids undesirable side effects of both drugs. For example, side effects including psychosis and cognitive deficits associated with the administration of NMDAr antagonists may be lessened in severity and frequency through the use of controlled-release methods that shift the Tmax to longer times, thereby reducing the dC/dT of the drug. Reducing the dC/dT of the drug not only increases Tmax, but also reduces the drug concentration at Tmax and reduces the Cmax/Cmean ratio providing a more constant amount of drug to the subject being treated over a given period of time and reducing adverse events associated with dosing. Similarly, side effects associated with the use of AChEIs may also be reduced in severity and frequency through controlled release methods.

In certain embodiments, the combinations provide additive effects. Additivity is achieved by combining the active agents without requiring controlled release technologies. In other embodiments, particularly when the pharmacokinetic profiles of the combined active pharmaceutical ingredients are dissimilar, controlled release formulations optimize the pharmacokinetics of the active pharmaceutical agents to reduce the variability of the Cratio over time. Reduction of Cratio variability over a defined time period enables a concerted effect for the agents over that time, maximizing the effectiveness of the combination. The Cratio variability ("Cratio.var") is defined as the standard deviation of a series of Cratios taken over a given period of time divided by the mean of those Cratios multiplied by 100%. The Cratio for the controlled release formulation of drugs with significantly different pharmacokinetic properties is more consistent than for the IR administration of the same drugs over any significant time period, including shortly after administration and at steady state.

Modes of Administration

The combination of the invention may be administered in either a local or systemic manner or in a depot or sustained release fashion. The two agents may be delivered in an oral, transdermal or intranasal formulation. In a preferred embodiment, the NMDAr antagonist, the AChEI of the combination, or both agents may be formulated to provide controlled, extended release (as described herein). For example, a pharmaceutical composition that provides controlled release of the NMDAr antagonist, the AChEI, or both may be prepared by combining the desired agent or agents with one or more additional ingredients that, when administered to a subject, causes the respective agent or agents to be released at a targeted rate for a specified period of time. The two agents are preferably administered in a manner that provides the desired effect from the first and second agents in the combination. Optionally, the first and second agents are admixed into a single formulation before they are introduced into a subject. The combination may be conveniently sub-divided in unit doses containing appropriate quantities of the first and second agents. The unit dosage form may be, for example, a capsule or tablet itself or it can be an appropriate number of such compositions in package form. The quantity of the active ingredients in the unit dosage forms may be varied or adjusted according to the particular need of the condition being treated.

Alternatively, the NMDAr antagonist and the AChEI of the combination may not be mixed until after they are introduced into the subject. Thus, the term "combination" encompasses embodiments where the NMDAr antagonist and the AChEI are provided in separate formulations and are administered sequentially. For example, the NMDAr antagonist and the AChEI may be administered to the subject separately within 2 days, 1 day, 18 hours, 12 hours, one hour, a half hour, 15 minutes, or less of each other. Each agent may be provided in multiple, single capsules or tablets that are administered separately to the subject. Alternatively, the NMDAr antagonist and the AChEI are separated from each other in a pharmaceutical composition such that they are not mixed until after the pharmaceutical composition has been introduced into the subject. The mixing may occur just prior to administration to the subject or well in advance of administering the combination to the subject.

If desired, the NMDAr antagonist and the AChEI may be administered to the subject in association with other therapeutic modalities, e.g., drug, surgical, or other interventional treatment regimens. Accordingly, the combination described herein may be administered simultaneously or within 14 days, 7 days, 5 days, 3 days, one day, 12 hours, 6 hours, 3 hours, or one hour of additional therapeutic modalities. Where the combination includes a non-drug treatment, the non-drug treatment may be conducted at any suitable time so long as a beneficial effect from the co-action of the combination and the other therapeutic modalities is achieved. For example, in appropriate cases, the beneficial effect is still achieved when the non-drug treatment is temporally removed from the administration of the therapeutic agents, perhaps by days or even weeks.

The preparation of pharmaceutical or pharmacological compositions are known to those of skill in the art in light of the present disclosure. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragées, gels, slurries, ointments, solutions suppositories, injections, inhalants and aerosols are examples of such formulations.

In some embodiments, the first agent and second agent of the combination described herein are provided within a single or separate pharmaceutical compositions. "Pharmaceutically or Pharmacologically Acceptable" includes molecular entities and compositions that do not produce an adverse, allergic or other untoward reaction when administered to an animal, or a human, as appropriate. "Pharmaceutically Acceptable Carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. "Pharmaceutically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Formulations for Oral Administration

Combinations can be provided as pharmaceutical compositions that are optimized for particular types of delivery. For example, pharmaceutical compositions for oral delivery are formulated using pharmaceutically acceptable carriers that are well known in the art and described further below. The carriers enable the agents in the combination to be formulated, for example, as a tablet, pill, capsule, solution, suspension, powder, liquid, or gel for oral ingestion by the subject.

The NMDAr antagonist, the AChEI of the invention, or both agents may be provided in a controlled, extended release form. In one example, at least 50%, 90%, 95%, 96%, 97%, 98%, 99%, or even in excess of 99% of the NMDAr antagonist is provided in an extended release dosage form. A release profile, i.e., the extent of release of the NMDAr antagonist or the AChEI over a desired time, may be conveniently determined for a given time by calculating the $C_{max}/C_{mean}$ for a desired time range to achieve a given acute or chronic steady state serum concentration profile. Thus, upon the administration to a subject (e.g., a mammal such as a human), the NMDAr antagonist has a Cmax/Cmean of approximately 2.5, 2, 1.5, or 1.0 approximately 1, 1.5, 2 hours to at least 6, 8, 9, 12, 18, 21, or 24 hours following such administration. If desired, the release of the NMDAr antagonist may be monophasic or multiphasic (e.g., biphasic). Moreover, the AChEI may be formulated as an extended release composition, having a $C_{max}/C_{mean}$ of approximately 2.5, 2, 1.5, or 1.0, approximately 1, 1.5, 2 hours to at least 6, 8, 9, 12, 18, 21, or 24 hours following administration to a subject. One of ordinary skill in the art can prepare combinations with a desired release profile using the NMDAr antagonists and the AChEI and formulation methods known in the art or described below.

As shown in Tables 1 and 2, the pharmacokinetic half-lives of the drugs of both classes vary from about 1.5 hours to 70 hours. Thus, suitable formulations may be conveniently selected to achieve nearly constant concentration profiles over an extended period (preferably from 8 to 24 hours) thereby maintaining both agents in a constant ratio and concentration for optimal therapeutic benefits for both acute and chronic administration. Preferred Cratio,var values may be less than about 30%, 50%, 75%, 90% of those for IR administration of the same active pharmaceutical ingredients over the first 4, 6, 8, or 12 hours after administration. Preferred Cratio,var values are less than about 100%, 70%, 50%, 30%, 20%, 10%.

Formulations that deliver this constant, measurable profile also allow one to achieve a monotonic ascent from an acute ratio to a desired chronic ratio for drugs with widely varying elimination half-lives. Compositions of this type and methods of treating patients with these compositions are embodiments of the invention. Numerous ways exist for achieving the desired release profiles, as exemplified below.

In some embodiments, the first agent and second agent of the combination described herein are provided within a single or separate pharmaceutical compositions. "Pharmaceutically or Pharmacologically Acceptable" includes molecular entities and compositions that do not produce an adverse, allergic or other untoward reaction when administered to an animal, or a human, as appropriate. "Pharmaceutically Acceptable Carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. "Pharmaceutically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable methods for preparing combinations in which the first agent, AChel, or both agents are provided in extended release-formulations include those described in U.S. Pat. No. 4,606,909 (hereby incorporated by reference). This reference describes a controlled release multiple unit formulation in which a multiplicity of individually coated or microencapsulated units are made available upon disintegration of the formulation (e.g., pill or tablet) in the stomach of the animal (see, for example, column 3, line 26 through column 5, line 10 and column 6, line 29 through column 9, line 16). Each of these individually coated or microencapsulated units contains cross-sectionally substantially homogenous cores containing particles of a sparingly soluble active substance, the cores being coated with a coating that is substantially resistant to gastric conditions but which is erodable under the conditions prevailing in the small intestine.

The combination may alternatively be formulated using the methods disclosed in U.S. Pat. No. 4,769,027, for example. Accordingly, extended release formulations involve prills of pharmaceutically acceptable material (e.g., sugar/starch, salts, and waxes) may be coated with a water permeable polymeric matrix containing an NMDAr antagonist and next overcoated with a water-permeable film containing dispersed within it a water soluble particulate pore forming material.

One or both agents of the combination may additionally be prepared as described in U.S. Pat. No. 4,897,268, involving a biocompatible, biodegradable microcapsule delivery system. Thus, the NMDAr antagonist may be formulated as a composition containing a blend of free-flowing spherical particles obtained by individually microencapsulating quantities of memantine, for example, in different copolymer excipients which biodegrade at different rates, therefore releasing memantine into the circulation at a predetermined rates. A quantity of these particles may be of such a copolymer excipient that the core active ingredient is released quickly after administration, and thereby delivers the active ingredient for an initial period. A second quantity of the particles is of such type excipient that delivery of the encapsulated ingredient begins as the first quantity's delivery begins to decline. A third quantity of ingredient may be encapsulated with a still different excipient which results in delivery beginning as the delivery of the second quantity beings to decline. The rate of delivery may be altered, for example, by varying the lactide/glycolide ratio in a poly(D,L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides.

In one embodiment of the invention, the NMDAr antagonist, the AChel, or both agents may be provided in a controlled or extended release form with or without an immediate release component in order to maximize the therapeutic benefit of each, while reducing unwanted side effects associated with each. When these drugs are provided in an oral form without the benefit of controlled or extended release components, they are released and transported into the body fluids over a period of minutes to several hours. Thus, the composition of the invention may contain an NMDAr antagonist and a sustained release component, such as a coated sustained release matrix, a sustained release matrix, or a sustained release bead matrix. In one example, memantine (e.g., 5-80 mg) is formulated without an immediate release component using a polymer matrix (e.g., Eudragit), Hydroxypropyl methyl cellulose (HPMC) and a polymer coating (e.g., Eudragit). Such formulations are compressed into solid tablets or granules or formed into pellets for capsules or tablets. Optionally, a coating such as Opadry® or Surelease® is used.

Separately prepared pellets, preferably release controlling pellets, combined in any manner provide the flexibility of making ratios of NMDAr antagonist to AChel containing compositions ranging from 0.1:100 to 100:0.1, more preferably from 1:100 to 100:1, most preferably 1:10 to 10:1 by mass or by numbers of pellets (see Example 7), and at the desired release profiles for each of the active ingredients. Optionally, the NMDAr antagonist, the AChel, or both agents are prepared using the OROS® technology, described for example, in U.S. Pat. Nos. 6,919,373, 6,923,800, 6,929,803, 6,939,556, and 6,930,128, all of which are hereby incorporated by reference. This technology employs osmosis to provide precise, controlled drug delivery for up to 24 hours and can be used with a range of compounds, including poorly soluble or highly soluble drugs. OROS® technology can be used to deliver high drug doses meeting high drug loading requirements. By targeting specific areas of the gastrointestinal tract, OROS® technology may provide more efficient drug absorption and enhanced bioavailability. The osmotic driving force of OROS® and protection of the drug until the time of release eliminate the variability of drug absorption and metabolism often caused by gastric pH and motility.

Alternatively, the combination may be prepared as described in U.S. Pat. No. 5,395,626 features a multilayered controlled release pharmaceutical dosage form. The dosage form contains a plurality of coated particles wherein each has multiple layers about a core containing an NMDAr antagonist and/or the AChel whereby the drug containing core and at least one other layer of drug active is overcoated with a controlled release barrier layer therefore providing at least two controlled releasing layers of a water soluble drug from the multilayered coated particle.

By way of example, extended release oral formulation can be prepared using additional methods known in the art. For example, a suitable extended release form of the either active pharmaceutical ingredient or both may be a matrix tablet composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm dil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable insoluble matrix polymers include ethyl cellulose, cellulose acetate butyrate, cellulose acetates, polymethacrylates containing quaternary ammonium groups or other pharmaceutically acceptable polymers. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticised according to the properties of the coating blend such as the glass transition temperature of the main agent or mixture of agents or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

The pharmaceutical composition described herein may also include a carrier such as a solvent, dispersion media, coatings, antibacterial and antifungal agents, isotonic and absorption delaying agents. The use of such media and agents for pharmaceutically active substances is well known in the art. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, may also be used as a carrier.

Additional methods for making controlled release formulations are described in, e.g., U.S. Pat. Nos. 5,422,123; 5,601,845; 5,912,013; and 6,194,000, all of which are hereby incorporated by reference.

Formulations for Other Routes of Administration

Alternatively, the compositions of the present invention may be administered transdermally. Preparation for delivery in a transdermal patch can be performed using methods also known in the art, including those described generally in, e.g., U.S. Pat. Nos. 5,186,938; 6,183,770; 4,861,800; 4,284,444 and WO 89/09051. A patch is a particularly useful embodiment in cases where the therapeutic agent has a short half-life or requires reduction in dC/dT. Patches can be made to control the release of skin-permeable active ingredients over a 12 hour, 24 hour, 3 day, and 7 day period. In one example, a 2-fold daily excess of an NMDAr antagonist is placed in a non-volatile fluid along with the opiate narcotic agent, non-steroidal anti-inflammatory agent, or anesthetic. Given the amount of the agents employed herein, a preferred release will be from 12 to 72 hours.

Transdermal preparations of this form will contain from 1% to 50% active ingredients. The compositions of the invention are provided in the form of a viscous, non-volatile liquid. Preferably, both members of the combination will have a skin penetration rate of at least $10^{-9}$ mole/cm$^2$/hour. At least 5% of the active material will flux through the skin within a 24 hour period. The penetration through skin of specific formulations may be measures by standard methods in the art (for example, Franz et al., J. Invest. Derm. 64:194-195 (1975)).

Pharmaceutical compositions containing the NMDAr antagonist and/or AChel of the combination may also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage may be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

In some embodiments, for example, the composition may be delivered intranasally to the cribriform plate rather than by inhalation to enable transfer of the active agents through the olfactory passages into the CNS and reducing the systemic administration. Devices used for this route of administration are included in U.S. Pat. No. 6,715,485. Compositions delivered via this route may enable increased CNS dosing or reduced total body burden reducing systemic toxicity risks associated with certain drugs.

Additional formulations suitable for other modes of administration include rectal capsules or suppositories. For suppositories, traditional binders and carriers may include, for example, polyalkylene glycols or triglycerides; such suppositories may be formed from mixtures containing the active ingredient in the range of 0.5% to 10%, preferably 1%-2%.

The combination may optionally be formulated for delivery in a vessel that provides for continuous long-term delivery, e.g., for delivery up to 30 days, 60 days, 90 days, 180 days, or one year. For example the vessel can be provided in a biocompatible material such as titanium. Long-term delivery formulations are particularly useful in subjects with chronic conditions, for assuring improved patient compliance, and for enhancing the stability of the combinations.

Formulations for continuous long-term delivery are provided in, e.g., U.S. Pat. Nos. 6,797,283; 6,764,697; 6,635,268, and 6,648,083.

If desired, the agents may be provided in a kit/as a combined preparation. The kit/combined preparation can additionally include instructions for use. In some embodiments, the kit/combined preparation includes in one or more containers the NMDAr antagonist and, separately, in one or more containers, the AChel described herein. The NMDAr antagonist and AChel may be mixed together prior to administration or may be administered separately to the subject. Where they are administered separately to the patient they may be administered at the same time as separate formulations, at different times and over different periods of time, which may be separate from one another or overlapping. The NMDAr antagonist and AChel may be administered in any order.

In other embodiments, the kit/combined preparation provides a combination with the NMDAr antagonist and the AChel mixed in one or more containers. The kits/combined preparations include a therapeutically effective dose of an agent for treating dementia or other CNS-related condition.

Preparation of a pharmaceutical composition for delivery in a subdermally implantable device can be performed using methods known in the art, such as those described in, e.g., U.S. Pat. Nos. 3,992,518; 5,660,848; and 5,756,115.

Indications Suitable for Treatment with the Combination

Any subject experiencing or at risk of experiencing a CNS-related disorder including dementia (e.g., Alzheimer's disease, Parkinson's disease, Picks disease, fronto-temporal dementia, vascular dementia, normal pressure hydrocephalus, HD, and MCI), neuro-related conditions, dementia-related conditions, such as epilepsy, seizure disorders, acute pain, chronic pain, chronic neuropathic pain may be treated using the combinations and methods described herein. Epileptic conditions include complex partial, simple partial, partials with secondary generalization, generalized—including absence, grand mal (tonic clonic), tonic, atonic, myoclonic, neonatal, and infantile spasms. Additional specific epilepsy syndromes are juvenile myoclonic epilepsy, Lennox-Gastaut, mesial temporal lobe epilepsy, nocturnal frontal lobe epilepsy, progressive epilepsy with mental retardation, and progressive myoclonic epilepsy. The combinations of the invention are also useful for the treatment and prevention of pain caused by disorders including cerebrovascular disease, motor neuron diseases (e.g., ALS, Spinal motor atrophies, Tay-Sach's, Sandoff disease, familial spastic paraplegia), neurodegenerative diseases (e.g., familial Alzheimer's disease, prion-related diseases, cerebellar ataxia, Friedrich's ataxia, SCA, Wilson's disease, RP, ALS, Adrenoleukodystrophy, Menke's Sx, cerebral autosomal dominant arteriopathy with subcortical infarcts (CADASIL); spinal muscular atrophy, familial ALS, muscular dystrophies, Charcot Marie Tooth diseases, neurofibromatosis, von-Hippel Lindau, Fragile X, spastic paraplesia, psychiatric disorders (e.g., panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence (e.g., alcohol, psychostimulants (eg, crack, cocaine, speed, meth), opioids, and nicotine), Tuberous sclerosis, and Wardenburg syndrome), strokes (e.g., thrombotic, embolic, thromboembolic, hemmorhagic, venoconstrictive, and venous), movement disorders (e.g., PD, dystonias, benign essential tremor, tardive dystonia, tardive dyskinesia, and Tourette's syndrome), ataxic syndromes, disorders of the sympathetic nervous system (e.g., Shy Drager, Olivopontoicerebellar degeneration, striatonigral degenration, PD, HD, Gullian Barre, causalgia, complex regional pain syndrome types I and II, diabetic neuropathy, and alcoholic neuropathy), Cranial nerve disorders (e.g., Trigeminal neuropathy, trigeminal neuralgia, Menier's syndrome, glossopharangela neuralgia, dysphagia, dysphonia, and cranial nerve palsies), myelopethies, traumatic brain and spinal cord injury, radiation brian injury, multiple sclerosis, Post-menengitis syndrome, prion diseases, myelities, radiculitis, neuropathies (e.g., Guillian-Barre, diabetes associated with dysproteinemias, transthyretin-induced neuropathies, neuropathy associated with HIV, neuropathy associated with Lyme disease, neuropathy associated with herpes zoster, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy), axonic brain damage, encephalopathies, and chronic fatigue syndrome. All of the above disorders may be treated with the combinations and methods described herein.

Administration of the Compositions

Immediate release formulations of memantine (e.g., Namenda) are typically administered at low doses (e.g., 5 mg/day) and progressively administered at increasing frequency and dose over time to reach a steady state serum concentration that is therapeutically effective. According to the manufacturer's recommendation, Namenda, an immediate release formulation of memantine, is first administered to subjects at a dose of 5 mg per day. After a period of time, subjects are administered with this dose twice daily. Subjects are next administered with a 5 mg and 10 mg dosing per day and finally administered with 10 mg Namenda twice daily. Using this approved dosing regimen, a therapeutically effective steady state serum concentration may be achieved within about thirty days following the onset of therapy. Using a sustained release formulation (at a constant daily dose of 22.5 mg, for example), a therapeutically effective steady state concentration may be achieved substantially sooner, without using a dose escalating regimen. Such concentration is predicted to be achieved within 13 days of the onset of therapy. Furthermore, the slope during each absorption period for the sustained release formulation is less (i.e. not as steep) as the slope for Namenda. Accordingly, the dC/dt of the sustained release formulation is reduced relative to the immediate release formulation even though the dose administered is larger than for the immediate release formulation. Based on this model, a sustained release formulation of memantine may be administered to a subject in an amount that is approximately the full strength dose (or that effectively reaches a therapeutically effective dose) from the onset of therapy and throughout the duration of treatment. Accordingly, a dose escalation would not be required. Similarly, the controlled release methods described herein may be employed to reduce the dC/dT for other NMDAr antagonists or ACheIs enabling the administration of the combinations without the requirement for dose escalation.

Treatment of a subject with the combination may be monitored using methods known in the art. The efficacy of treatment using the combination is preferably evaluated by examining the subject's symptoms in a quantitative way, e.g., by noting a decrease in the frequency of adverse symptoms, behaviors, or attacks, or an increase in the time for sustained worsening of symptoms. In a successful treatment, the subject's status will have improved (i.e., frequency of relapses will have decreased, or the time to sustained progression will have increased).

The invention will be illustrated in the following non-limiting examples.

Example 1

In vivo Method for Determining Optimal Steady-State Concentration Ratio ($C_{ratio,ss}$)

A dose ranging study is performed using, for example, the dementia model (APP23 mouse model described by Van Dam et al. (See Psychopharmacology 2005, 180(1):177-190), or the Tg2576 model described by Dong et al (Psychopharmacology 2005, 181(1):145-152). An isobolic experiment ensues in which the drugs are combined in fractions of their EDXXs to add up to ED100 (e.g., ED50:ED50 or ED25:ED75). The plot of the data is constructed. The experiment points that lie below the straight line between the ED50 points on the graph are indicative of synergy, points on the line are indicative of additive effects, and points above the line are indicative of inhibitory effects. The point of maximum deviation from the isobolic line is the optimal ratio. This is the optimal steady state ratio (Cratio,ss) and is adjusted based upon the agents half-life. Similar protocols may be applied in a wide variety of validated animal models.

Example 2

Combinations of an NMDAr Antagonist and an AChel

Representative combination ranges and ratios are provided below for compositions of the invention. The ranges given in Table 3 are based on the formulation strategies described herein.

Example 3

Release Profile of Memantine and Galantamine

Release proportions are shown in Table 4 below for a combination of memantine and galantamine. The cumulative fraction is the amount of drug substance released from the formulation matrix to the serum or gut environment (e.g., U.S. Pat. No. 4,839,177) or as measured with a USP II Paddle system using water as the dissolution medium.

TABLE 4

Release profile of memantine and donepezil

| Time | MEMANTINE $T^{1}/_{2}$ = 60 hrs cum. fraction A | GALANTAMINE $T^{1}/_{2}$ = 7 hrs cum. fraction B |
|---|---|---|
| 1 | 0.2 | 0.2 |
| 2 | 0.3 | 0.3 |
| 4 | 0.4 | 0.4 |
| 8 | 0.5 | 0.5 |
| 12 | 0.6 | 0.6 |
| 16 | 0.7 | 0.7 |
| 20 | 0.8 | 0.8 |
| 24 | 0.9 | 1.0 |

Example 4

Tablet Containing a Combination of Memantine and Galantamine

An extended release dosage form for administration of memantine and galantamine is prepared as three individual compartments. Three individual compressed tablets are prepared, each having a different release profile, are encapsulated into a gelatin capsule which is then closed and sealed. The components of the three tablets are as follows.

TABLE 5

Immediate Release Dosage form

| Component TABLET 1 (immediate release): | Function | Amount per tablet |
|---|---|---|
| Memantine | Active agent | 0 mg |
| Galantamine HBr | Active agent | 10.25 mg |
| Dicalcium phosphate dihydrate | Diluent | 26.6 mg |

TABLE 3

Adult Dosage and Ratios for Combination Therapy

| | AcheI Quantity, mg/day/(AChel:NMDA Ratio Range) | | | | | |
|---|---|---|---|---|---|---|
| NMDA drug mg/day | Donepezil/ ARICEPT ® | Rivastigmine/ EXELON ® | Galantmine/ REMINYL ® | Tacrine/ COGNEX ® | Huperzine-A | Metrifonate |
| Memantine/ 2.5–80 | 1–20 (0.012–8) | 1–24 (0.012–9.6) | 3–48 (0.038–19) | 8–160 (0.1–64) | 0.02–0.8 (0.0025–0.32) | 8–80 (0.1–32) |
| Amantadine/ 50–400 | 1–20 (0.0025–0.4) | 1–24 (0.0025–0.48) | 3–48 (0.0075–0.96) | 8–160 (0.02–3.2) | 0.02–0.8 (0.0005–0.016) | 8–80 (0.02–1.6) |
| Rimantadine/ 50–200 | 1–20 (0.005–0.4) | 1–24 (0.005–0.48) | 3–48 (0.015–0.96) | 8–160 (0.04–3.2) | 0.02–0.8 (0.0001–0.016) | 8–80 (0.04–1.6) |

TABLE 5-continued

Immediate Release Dosage form

| Component TABLET 1 (immediate release): | Function | Amount per tablet |
|---|---|---|
| Microcrystalline cellulose | Diluent | 26.6 mg |
| Sodium starch glycolate | Disintegrant | 1.2 mg |
| Magnesium Stearate | Lubricant | 0.6 mg |

TABLE 6

Delayed Release (3–5 hours) Dosage form

| Component TABLET 2 (3–5 hour release): | Function | Amount per tablet |
|---|---|---|
| Memantine | Active agent | 10 mg |
| Galantamine HBr | Active agent | 10.25 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |
| Eudragit RS30D | Delayed release | 4.76 mg |
| Talc | Coating component | 3.3 mg |
| Triethyl citrate | Coating component | 0.95 mg |

TABLE 7

Delayed Release (7–10 hours) Dosage form

| Component TABLET 3 (Release delayed 7–10 hours): | Function | Amount per tablet |
|---|---|---|
| Memantine | Active agent | 12.5 mg |
| Galantamine HBr | Active agent | 5.125 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |
| Eudragit RS30D | Delayed release | 6.5 mg |
| Talc | Coating component | 4.4 mg |
| Triethyl citrate | Coating component | 1.27 mg |

The tablets are prepared by wet granulation of the individual drug particles and other core components as may be done using a fluid-bed granulator, or are prepared by direct compression of the admixture of components. Tablet 1 (Table 5) is an immediate release dosage form, releasing the active agents within 1-2 hours following administration. It contains no memantine to avoid the dC/dT effects of the current dosage forms. Tablets 2 (Table 6) and 3 (Table 7) are coated with the delayed release coating material as may be carried out using conventional coating techniques such as spray-coating or the like. The specific components listed in the above tables may be replaced with other functionally equivalent components, e.g., diluents, binders, lubricants, fillers, coatings, and the like.

Oral administration of the capsule to a patient will result in a release profile having three pulses, with initial release of galantamine from the first tablet being substantially immediate, release of the memantine and galantamine from the second tablet occurring 3-5 hours following administration, and release of the memantine and galantamine from the third tablet occurring 7-10 hours following administration.

Example 5

Pellets Containing Memantine or Donepezil

Memantine HCl (or Donepezil HCl) containing pellets were prepared by wet massing. Memantine HCl (or Donepezil HCl) was weighed and sieved through a No. 20 screen into the bowl of low shear planetary mixer. To this, microcrystalline cellulose was weighed and added through No. 20 screen and blended with Memantine HCl (or Donepezil HCl) using a spatula, then in a planetary mixer on low speed. Eudragit NE 400, accurately weighed was incrementally added to the powder blend, allowing sufficient time between additions for complete distribution. To avoid accumulation at the bottom and to loosen the material, the bottom was periodically scraped. Purified water was blended into the mixture in 10 mL increments (the first of which was used to rinse the beaker containing Eudragit NE 40D) until a uniform blend appropriate for extrusion was obtained. Experimental batches were prepared with 10 to 50 ml water. Wet massing was followed by extrusion, spheronization and drying by procedures well known in the prior art.

TABLE 8

Pellets containing Memantine HCl

| Component | Supplier | Percent in Formula[1] | Wt. solid per Batch (grams) | Target Wt. per Batch (g) | Actual Wt. per Batch (g) |
|---|---|---|---|---|---|
| Memantine HCl | | 20.0% | 50.0 | 50.0 | 50.00 |
| Eudragit NE 40D | Degussa | 30.0% | 75.0 | 187.5 | 187.50 |
| Microcrystalline Cellulose (Avicel PH 101) | FMC Corp | 50.0% | 125.0 | 125.0 | 125.00 |
| Purified Water | | N/A | N/A | 50.0 | 10.0 |
| TOTAL | | 100.0% | 250.0 | N/A | N/A |

[1]based on solid in the final product

TABLE 9

Pellets containing Donepezil HCl

| Component | Supplier | Percent in Formula[1] | Wt. solid per Batch (grams) | Target Wt. per Batch (g) | Actual Wt. per Batch (g) |
|---|---|---|---|---|---|
| Donepezil HCl | | 20.0% | 40.0 | 40.0 | 39.98 |
| Eudragit NE 40D | Degussa | 30.0% | 60.0 | 150.0 | 150.05 |

TABLE 9-continued

| Pellets containing Donepezil HCl | | | | | |
|---|---|---|---|---|---|
| Component | Supplier | Percent in Formula[1] | Wt. solid per Batch (grams) | Target Wt. per Batch (g) | Actual Wt. per Batch (g) |
| Microcrystalline Cellulose (Avicel PH 101) | FMC Corp | 50.0% | 100.0 | 100.0 | 100.00 |
| Purified Water | | N/A | N/A | 50.0 | 10.0 |
| | TOTAL | 100.0% | 200.0 | N/A | N/A |

[1]based on solid in the final product

Example 6

Memantine HCl/Donepezil HCl Formulations

Formulations of Sustained Release (SR) Memantine HCl (or Donepezil HCl), fast and medium, were obtained by applying a subcoat of Opadry (2% final pellet weight) followed by a functional coating of Surelease (15% dispersion prepared from 25% Surelease) to 20% Memantine HCl (or Donepezil HCl) pellets.

Formulations of Sustained Release (SR) Memantine HCl (or Donepezil HCl), slow, were obtained by applying a subcoat of Opadry (10% final bead weight), functional coating of plasticized Eudragit RS (35% final pellet weight) and triethylcitrate (plasticizer, 10% of the functional coating) to 20% Memantine HCl (or Donepezil HCl) pellets.

TABLE 10

| Memantine SR Products | | | | | | |
|---|---|---|---|---|---|---|
| Product | SR Memantine Pellets (Fast) | | SR Memantine Pellets (Medium) | | SR Memantine Pellets (Slow) | |
| "Label Claim" (mg active/mg pellets) | 0.164 | | Blend of 40% "Fast" and 60% "Slow" | | 0.100 | |
| Sample weight (mg pellets) | 134.6 | 136.2 | | | 207.9 | 208.9 |
| 16 hr "Assay" Value (mg released) | 23.41 | 23.44 | | | 17.97 | 18.24 |
| "Assay" Value (mg active/mg pellets) | 0.174 | 0.172 | | | 0.0864 | 0.0873 |
| Average Assay Value (mg active/mg pellets) | 0.173 | | | | 0.0869 | |
| Amount of pellets for 22.5 mg dose (mg) | 130.0 | | 52.0 | 155.4 | 259.0 | |

TABLE 11

| Donepezil Immediate Release (IR) Product | | |
|---|---|---|
| Product | IR Donepezil HCl | |
| "Label Claim" (mg active/mg granulation) | 0.0357 | |
| Sample weight (mg pellets) | 140.6 | 143.7 |
| "Assay" Value (mg released) | 4.25 | 4.28 |
| "Assay" Value (mg active/mg granulation) | 0.0302 | 0.0298 |
| Average Assay Value (mg active/mg gran) | 0.030 | |
| Amount of granulation for 5 mg dose (mg) | 166.7 | |

TABLE 12

| Donepezil SR Product | | | | | | |
|---|---|---|---|---|---|---|
| Product | SR Donepezil HCl Pellets (Fast) | | SR Donepezil HCl Pellets (Medium) | | SR Donepezil HCl Pellets (Slow) | |
| "Label Claim" (mg active/mg pellets) | 0.180 | | 0.166 | | 0.156 | |
| Sample weight (mg pellets) | 113.8 | 113.9 | 135.6 | 135.5 | 128.8 | 128.3 |

TABLE 12-continued

| | Donepezil SR Product | | | | | |
|---|---|---|---|---|---|---|
| Product | SR Donepezil HCl Pellets (Fast) | | SR Donepezil HCl Pellets (Medium) | | SR Donepezil HCl Pellets (Slow) | |
| 16 hr "Assay" Value (mg released) | 20.03 | 20.00 | 23.26 | 23.46 | 19.27 | 19.86 |
| "Assay" Value (mg active/mg pellets) | 0.176 | 0.176 | 0.172 | 0.173 | 0.150 | 0.155 |
| Average Assay Value (mg active/mg pellets) | 0.176 | | 0.172 | | 0.152 | |
| Amount of pellets for 5 mg dose (mg) | 28.4 | | 29.0 | | 32.8 | |

Example 7

Dosage Formulation of Memantine-Donepezil Combination

Various combinations of memantine and donepezil were prepared by filling the respective pellets in hard gelatin capsules as shown in Table 13. The separately prepared pellets provide the flexibility of making ratios of memantine to donepezil pellets ranging from 0.1:100 to 100:0.1, more preferably from 1:100 to 100:1, most preferably 1:10 to 10:1.

TABLE 13

Memantine-Donepezil Dosage Combinations

| | Memantine | | Donepezil | |
|---|---|---|---|---|
| Product | Wt. solid/ dosage Unit (in mg) | Formulation | Wt. solid/ dosage Unit (in mg) | Formulation |
| NPI-6170 | 130.0 | SR (Fast) | 166.7 | IR |
| NPI-6270 | 52.0 155.4 | SR (Fast) SR (Slow) | 166.7 | IR |
| NPI-6370 | 259.0 | SR (Slow) | 166.7 | IR |
| NPI-6171 | 130.0 | SR (Fsst) | 28.4 | SR (Fast) |
| NPI-6271 | 52.0 155.4 | SR (Fast) SR (Slow) | 28.4 | SR (Fast) |
| NPI-6371 | 259.0 | SR (Slow) | 28.4 | SR (Fast) |
| NPI-6172 | 130.0 | SR (Fast) | 29.0 | SR (medium) |
| NPI-6272 | 52.0 155.4 | SR (Fast) SR (Slow) | 29.0 | SR (medium) |
| NPI-6372 | 259.0 | SR (Slow) | 29.0 | SR (medium) |
| NPI-6173 | 130.0 | SR (Fast) | 32.8 | SR (Slow) |
| NPI-6273 | 52.0 155.4 | SR (Fast) SR (Slow) | 32.8 | SR (Slow) |
| NPI-6373 | 259.0 | SR (Slow) | 32.8 | SR (Slow) |

SR = Sustained Release,
IR = Immediate Release

Example 8

Dissolution Profiles

The dissolution profiles of the various memantine-donepezil combinations (as shown in Example 7) were obtained from USP II (paddle) dissolution system at 50 rpm, at a temperature of 37.0±0.5° C., using water as the medium (FIGS. 2A-2C, 3A-3C, 4A-4C and 5A-5C).

For the dissolution analysis, 10 mL dissolution solutions of memantine and donepezil were diluted with 3 mL of 0.1% formic acid. Standards of memantine or donepezil were also prepared and diluted with 3 mL of 0.1% formic acid. A 1 mL aliquot of the diluted solution or standard was transferred into an HPLC vial. A 10 µL aliquot of the solution or standard was injected onto the LC/MS/MS for analysis. A C18 reversed phase column (Phenomenex, Luna 5µ, Phenyl-Hexyl 50×2 mm) was used for analysis. Memantine and donepezil were separated from endogenous interfering substances and subsequently eluted from the HPLC column by a mobile phase of 33% acetonitrile, 33% methanol and 34% formic acid for mass quantification. A mass spectrometer set at mass-to-charge ratios (m/z) of 180.51>162.70 and 380.14>288.18 was used to detect and quantify memantine and donepezil, respectively. Data were processed and calculated by an automated data acquisition system (Analyst 1.2, Applied Biosystems, Foster City, Calif.).

Example 9

Release Profiles of IR and SR Memantine-Donepezil Formulations

Figure 4A:
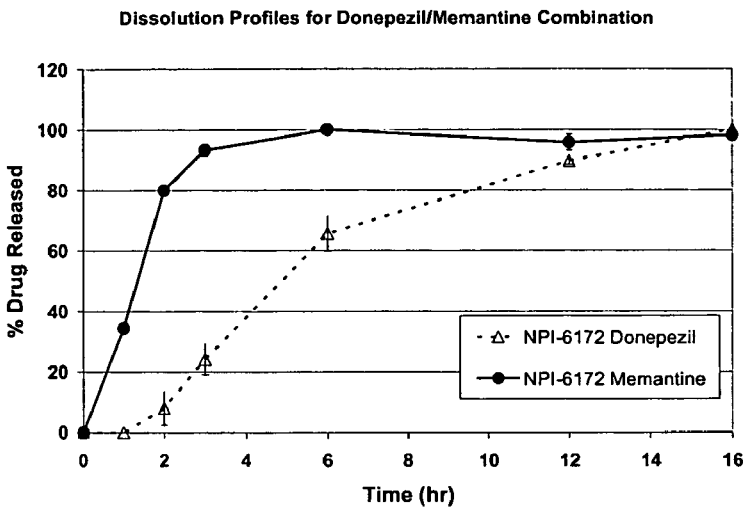
FIG. 4 shows dissolution profile of A) SR Memantine (fast)—SR Donepezil (medium) (NPI-6172), B) SR Memantine (medium)—SR Donepezil (medium) (NPI-6272), C) SR Memantine (slow)—SR Donepezil (medium) (NPI-6372).
Figure 4B:
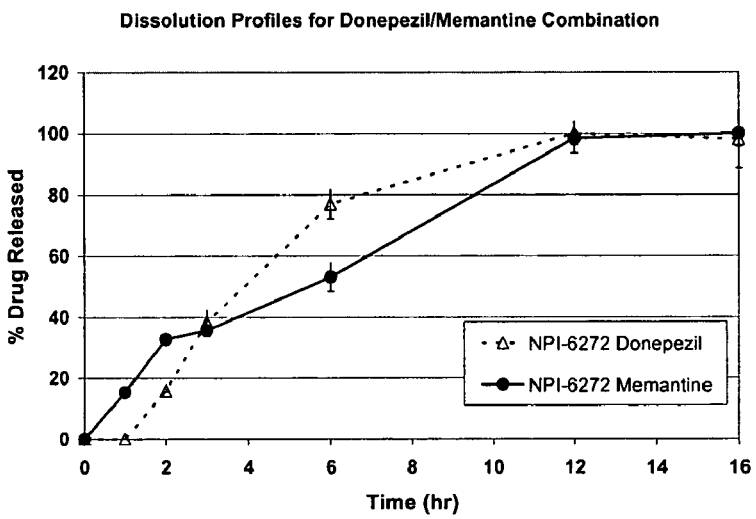
Figure 4C:
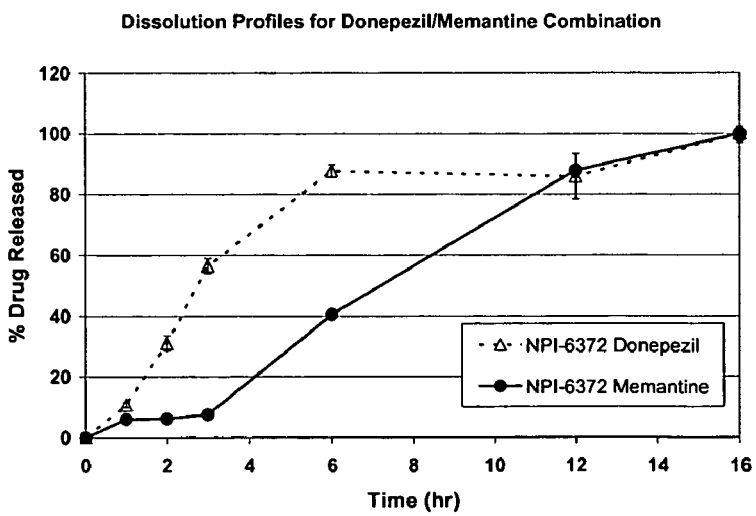
Figure 5A:
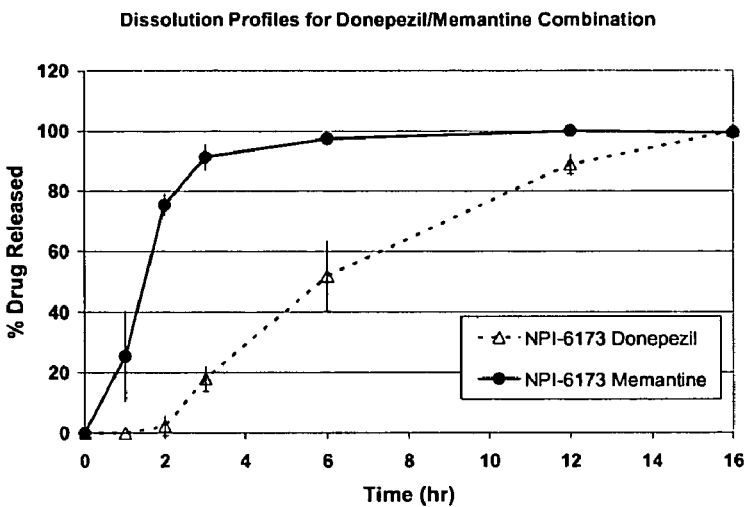
FIG. 5 shows dissolution profile of A) SR Memantine (fast)—SR Donepezil (slow) (NPI-6173), B) SR Memantine (medium)—SR Donepezil (Slow) (NPI-6273), C) SR Memantine (slow)—SR Donepezil (slow) (NPI-6373).
Figure 5B:
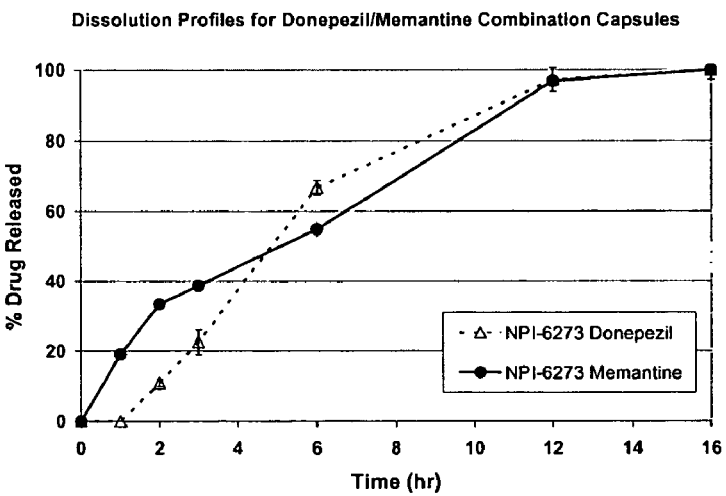
Figure 5C:
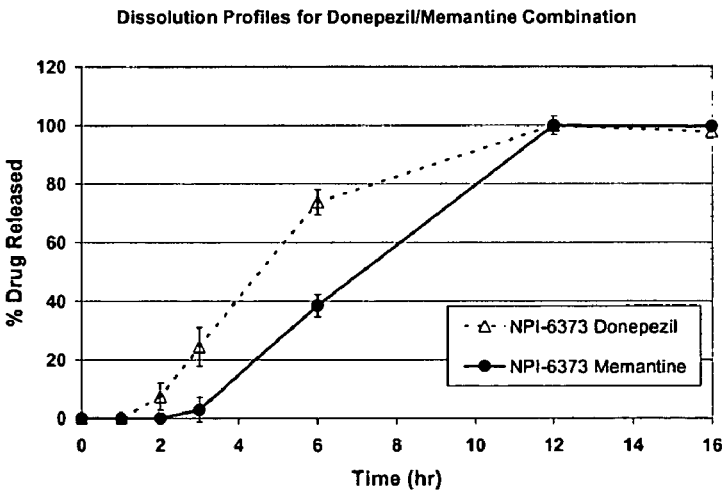
Figure 6A:
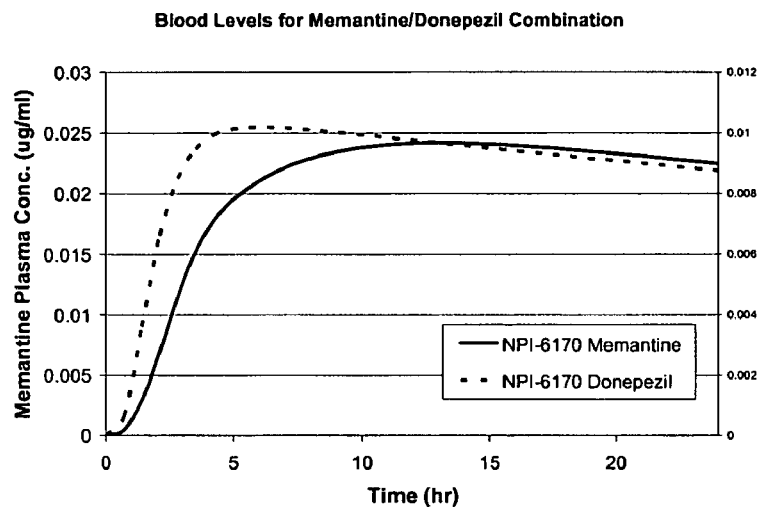
FIG. 6 shows plasma concentrations obtained using the GastroPlus software package v.4.0.2 for the following compositions: A) SR Memantine (fast)—IR Donepezil (NPI-6170), B) SR Memantine (fast)—SR Donepezil (Slow) (NPI-6173), C) SR Memantine (medium)—SR Donepezil (medium) (NPI-6272), D) SR Memantine (Slow)—IR Donepezil (NPI-6370), E) SR Memantine (Slow) SR Donepezil (slow) (NPI-6373).
Figure 6B:
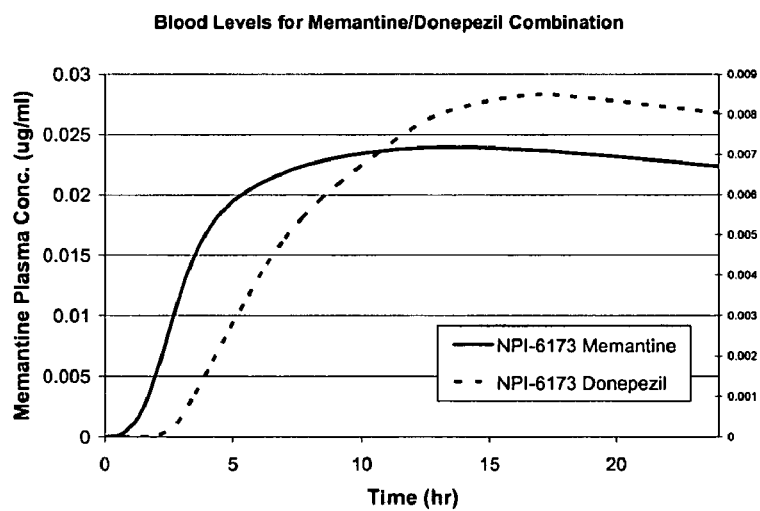
Figure 6C:
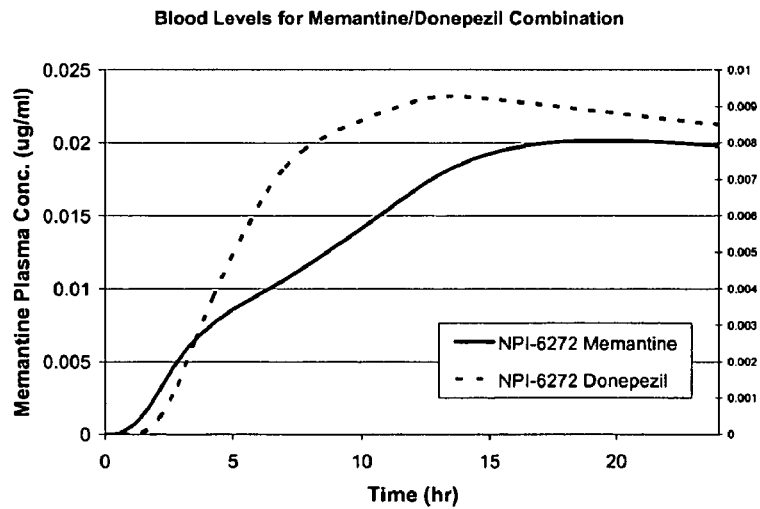
Figure 6D:
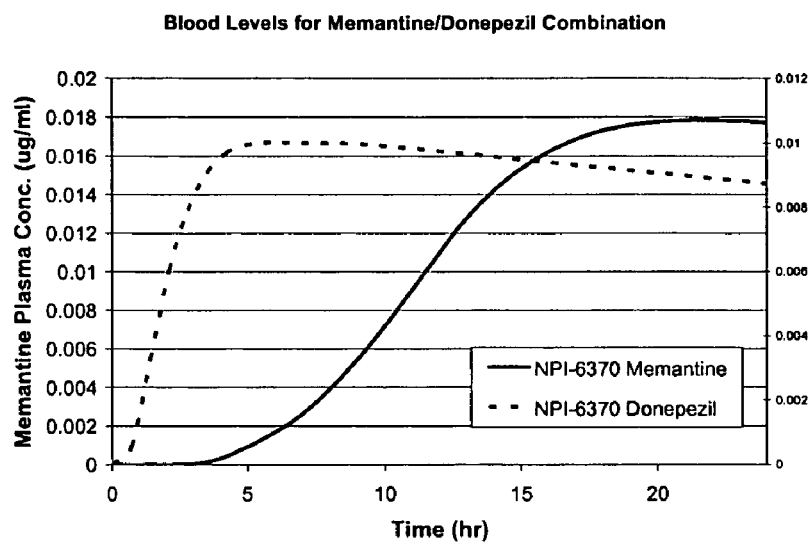
Figure 6E:
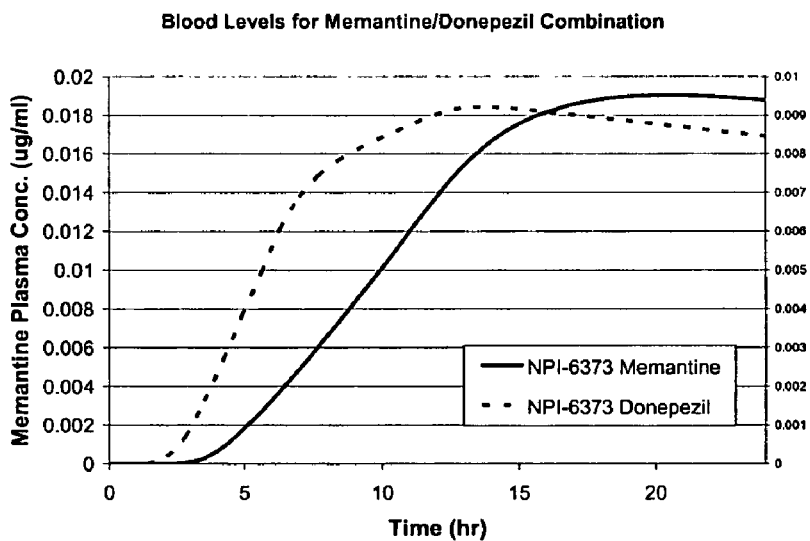

The in vivo release profiles were obtained using the Gastro-Plus software package v.4.0.2 (FIGS. 6A-6E, 7). Exemplary human PK release profiles are shown in FIG. 7. The release profiles and pharmacokinetic properties for a controlled release combination product made according to Examples 5-7 as compared to IR administration of presently marketed products are shown in FIG. 7 and the table in FIG. 8. For the IR administration, oral dosing is per the manufacturers' recommendation (5 mg memantine q.d., incremented on a weekly basis to 5 mg BID, 10 mg in the morning and 5 mg in the evening, and 10 mg memantine b.i.d.thereafter; 5 mg donepezil q.d for two weeks, increasing to 10 mg donepezil q.d. thereafter). For the SR formulation NPI-6272, the 22.5 mg memantine and 10 mg donepezil are provided in a controlled release oral delivery formulation releasing the active agents as shown in FIG. 4B. The SR product dC/dT is considerably lower than the IR form for a similar dose for both memantine and donepezil. As measured, the dC/dT for memantine at 22.5 mg is comparable to that for a 5 mg IR dosage form. Thus, the SR formulations provide a more gradual increase in the drug during each patient dose.

In addition to achieving the desired release profile, this combination formulation will exhibit a preferred decrease Cmax/Cmean, even with a higher dose of the NMDAr antagonist and AChEI, thus the present invention may provide greater doses for increased therapeutic effect without escalation that might otherwise be required. Furthermore, the increased dosing allows less frequent administration of the therapeutic agents.

Example 10

A Patch Providing Extended Release of Memantine and Rivastigmine

As described above, extended release formulations of an NMDAr antagonist are formulated for topical administration. Memantine transdermal patch formulations are prepared as described, for example, in U.S. Pat. Nos. 6,770,295 and 6,746,689.

For the preparation of a drug-in-adhesive acrylate, 5 g of memantine and 1 g of rivastigmine are dissolved in 10 g of ethanol and this mixture is added to 20 g of Durotak 387-2287 (National Starch & Chemical, U.S.A.). The drug gel is coated onto a backing membrane (Scotchpak 1012; 3M Corp., U.S.A.) using a coating equipment (e.g., RK Print Coat Instr. Ltd, Type KCC 202 control coater). The wet layer thickness is 400 µm. The laminate is dried for 20 minutes at room temperature and then for 30 minutes at 40° C. A polyester release liner is laminated onto the dried drug gel. The sheet is cut into patches and stored at 2-8° C. until use (packed in pouches). The concentration of memantine in the patches ranges between 5.6 and 8 mg/cm$^2$, while rivastigmine ranges between 1.1 and 1.6 mg/cm$^2$. The nearly continuous infusion of the components provides a much more consistent Cratio over time maximizing the additive or synergistic effects of the combinations of the present invention to achieve the optimal therapeutic effects.

Example 11

Multiple Dose Safety Study in Alzheimer's Patients with an Extended Release Memantine, Extended Release Donepezil Combination A study to determine safety and pharmacokinetics of an extended release combination formulation of memantine and donepezil is described below. The study results are expected to assess the frequency of adverse events as well as evaluate the pharmacokinetic parameters at higher doses.

| | |
|---|---|
| Purpose | To determine the safety and pharmacokinetics of repeated doses of drug. |
| Dosage: | Based on previous single ascending dose (SAD) study, either e.g. 22.5 mg memantine SR + 4 mg donepezil SR, 45 mg memantine SR + 4 mg donepezil SR, or 45 mg memantine SR + 8 mg donepezil SR, QD for 30 days |
| Concurrent Controls | memantine IR or memantine IR plus donepezil IR (both dosed as per manufacturers' labels) |
| Route: | Oral |
| Subject Population: | Males or females diagnosed with dementia of the Alzheimer's type. (Age range 50–80?) |
| Structure: | 4 arm |
| Study Sites: | TBD |
| Blinding: | Patients blinded |
| Method of Subject Assignment: | Random with equal number of males and females in each group and equal age distributions within groups |
| Total Sample Size: | 24 Subjects 6 per dosing arm |
| Primary Efficacy Endpoint: | None |
| Adverse Events: | Monitored at least twice daily for behavioral, cardiovascular, and gastrointestinal effects reported for high doses of memantine or donepezil (including dizziness, headache, confusion, constipation, hypertension, coughing, nausea, diarrhea, vomiting). |
| Blood Collection | By canula through first day of study period then 2-4 times daily for rest of study |
| Analysis | Assays to measure memantine, donepezil, and potentially other physiological parameters, adverse events |

Example 12

Treatment of Alzheimer's Patients with an Extended Release Memantine, Extended Release Donepezil Combination A study to determine effectiveness of two extended release combination formulations of memantine and donepezil is described below. The study results are expected to establish a more rapid onset of efficacy without increase in adverse effects (confirming tolerability of a non-dose escalating dosing regimen (i.e., administration of substantially identical doses of memantine and donepezil throughout the term of dosing)).

| | |
|---|---|
| Purpose | To determine the efficacy of combination therapy, non-dose escalated |
| Study Dosages: | 22.5 mg memantine SR + 4 mg donepezil SR, 45 mg memantine SR + 4 mg donepezil SR |
| Concurrent Controls | memantine IR (Namenda) or memantine IR plus donepezil IR (Aricept) both per manufacturers' dosing labels (as of 2004). |
| Route: | Oral |
| Subject Population: | Males or females diagnosed with dementia of the Alzheimer's type. (Age range 50–80) |
| Structure: | 4 arm |
| Study Sites: | Multi-center |
| Blinding: | Patients blinded |
| Method of Subject Assignment: | Random with equal number of males and females in each group and equal age distributions within groups |
| Total Sample Size: | 400 subjects, 100 per arm |
| Primary Efficacy Endpoint: | Improvement of ADAS-Cog, SIBIC, HAM-D in or neuropsychiatric index at 7, 14, 21, 42, 63, 84 days. |
| Efficacy Monitoring: | Monitored twice per week for first 4 weeks, then weekly thereafter. |
| Adverse Events: | Monitored at least twice daily for behavioral, cardiovascular and gastrointestinal effects reported for high doses of memantine or donepezil (including dizziness, headache, confusion, constipation, hypertension, coughing, nausea, diarrhea, vomiting). |
| Blood Collection: | By canula at the following time points: Day 1: 0, 4, 8, 12 hours Days 2, 4, 6, 8, 10, 12, 14, 17, 21, 28, 35, 42, 49, 56, 63, 70, 77, 84 pre-dose trough |
| Analysis: | Efficacy, adverse events, and laboratory assays measuring study drugs. |

What is claimed is:

1. A method of treating a CNS-related condition comprising orally administering once a day to a human subject in need thereof:
   (a) 5-40 mg memantine or a pharmaceutically acceptable salt thereof provided in an extended release dosage form, wherein said extended release memantine or pharmaceutically acceptable salt thereof provides a change in plasma concentration as a function of time (dC/dT) that is less than about 50% of the dC/dT of the same quantity of an immediate release form of memantine, wherein the dC/dT is measured in a single dose human PK study between the time period of 0 to Tmax of the immediate release form of memantine; and
   (b) a therapeutically effective amount of donepezil or a pharmaceutically acceptable salt thereof, wherein the CNS-related condition is selected from the group consisting of Alzheimer's disease and dementia.

2. The method of claim 1, wherein the amount of memantine or pharmaceutically acceptable salt thereof ranges between 10 to 40 mg per dose.

3. The method of claim 2, wherein the amount of memantine or pharmaceutically acceptable salt thereof ranges between 12.5 to 40 mg per dose.

4. The method of claim 1, wherein said memantine or a pharmaceutically acceptable salt thereof and said donepezil or a pharmaceutically acceptable salt thereof are administered simultaneously.

5. The method of claim 1, wherein said memantine or a pharmaceutically acceptable salt thereof and said donepezil or a pharmaceutically acceptable salt thereof are administered as a single composition.

6. A method of reducing the potential for an adverse effect in a human subject being treated for a CNS-related condition comprising orally administering once a day to a human subject in need thereof a pharmaceutical composition comprising:
   (a) 5-40 mg memantine or a pharmaceutically acceptable salt thereof in an extended release form, wherein said extended release memantine or pharmaceutically acceptable salt thereof provides a change in plasma concentration as a function of time (dC/dT) that is less than about 50% of the dC/dT of the same quantity of an immediate release form of memantine, wherein the dC/dT is measured in a single dose human PK study between the time period of 0 to Tmax of the immediate release form of memantine; and
   (b) donepezil or a pharmaceutically acceptable salts thereof, wherein the CNS-related condition is selected from the group consisting of Alzheimer's disease and dementia;
   and further wherein said adverse effect is related to memantine.

7. The method of claim 6, wherein the composition is in a unit dosage form comprising 10 to 40 mg of the memantine or pharmaceutically acceptable salt thereof.

8. The method of claim 6, wherein the donepezil or pharmaceutically acceptable salt thereof is in an immediate release form.

9. The method of claim 6, wherein the memantine or pharmaceutically acceptable salt thereof is formulated as beads and/or pellets.

10. The method of claim 9, wherein the beads and/or pellets comprise an extended release coating.

11. The method of claim 10, wherein the extended release coating comprises an insoluble matrix polymer and a water soluble material.

12. The method of claim 11, wherein the insoluble matrix polymer is ethyl cellulose.

13. The method of claim 11, wherein the insoluble matrix polymer is ethyl cellulose, and the water soluble material is selected from the group consisting of hydroxypropyl methyl cellulose and polyvinylpyrrolidone.

14. The method of claim 7, wherein the dosage form is in a capsule.

15. The method of claim 6, wherein the composition comprises 1 to 20 mg donepezil hydrochloride.

16. The method of claim 6, wherein administration of the composition to a human subject provides a shift in memantine $T_{max}$ of at least 8 hours relative to an immediate release form of memantine.

17. The method of claim 6, wherein administration of the composition to a human subject provides a memantine $T_{max}$ of at least 19 hours.

18. The method of claim 6, wherein administration of the composition to a human subject provides a plasma memantine concentration profile characterized by a maximum memantine plasma concentration to mean memantine plasma concentration ratio (Cmax/cmean) of about 2.5 to 2 at 1 hour to at least 6 hours after administration.

19. The method of claim 6, wherein said memantine or a pharmaceutically acceptable salt thereof and said donepezil or a pharmaceutically acceptable salt thereof are provided in a unit dosage form.

20. The method of claim 6, wherein the composition comprises at 12.5 mg to 40 mg memantine hydrochloride.

21. The method of claim 6, wherein the composition comprises at least 22.5 mg memantine hydrochloride and 1 to 20 mg of donepezil hydrochloride.

22. The method of claim 1, wherein said extended release memantine or a pharmaceutically acceptable salt thereof has an in vitro dissolution profile less than 30% in one hour, less than 40% in two hours, greater than 40% in six hours as measured using a USP type 2 (paddle) dissolution system at 50 rpm, at a temperature of 37±0.5° with water as a dissolution medium.

23. The method of claim 1, wherein at least 80% of the memantine or pharmaceutically acceptable salt thereof in the composition is provided in an extended release form, with the remainder in an immediate release form.

24. The method of claim 1, wherein at least 95% of the memantine or pharmaceutically acceptable salt thereof in the composition is provided in an extended release forms, with the remainder in an immediate release form.

25. The method of claim 1, wherein the release of the memantine or pharmaceutically acceptable salt thereof is monophasic.

26. The method of claim 1, wherein the release of the memantine or pharmaceutically acceptable salt thereof is biphasic.

27. The method of claim 1, wherein the memantine further comprises one or more extended release excipients selected from the group consisting of ethyl cellulose, hydroxypropyl methyl cellulose and polyvinylpyrrolidone.

28. The method of claim 6, wherein the composition comprises 20 mg to 40 mg of memantine.

29. The method of claim 6, wherein at least 80% of the memantine or pharmaceutically acceptable salt thereof in the composition is provided in an extended release form, with the remainder in an immediate release form.

30. The method of claim 6, wherein at least 95% of the memantine or pharmaceutically acceptable salt thereof in the composition is provided in an extended release forms, with the remainder in an immediate release form.

31. The method of claim 6, wherein the release of the memantine or pharmaceutically acceptable salt thereof is monophasic.

32. The method of claim 6, wherein the release of the memantine or pharmaceutically acceptable salt thereof is biphasic.

33. The method of claim 6, wherein the memantine further comprises one or more extended release excipients selected from the group consisting of ethyl cellulose, hydroxypropyl methyl cellulose and polyvinylpyrrolidone.

34. In a method of treating a subject for a CNS-related condition comprising administering to said subject a memantine drug selected from the group consisting of memantine and a pharmaceutically acceptable salt thereof, and a therapeutically effective amount of a donepezil drug selected from the group consisting of donepezil and a pharmaceutically acceptable salt thereof, the improvement comprising:
   (a) said memantine drug is administered in an extended release dosage form, wherein said extended release memantine provides a change in plasma concentration as a function of time (dC/dT) in a defined time period of 0 to Tmax of an immediate release form of memantine after administration, as measured in a human single dose PK study, that is less than about 50% of the change in plasma concentration (dC/dT) of the same quantity of said immediate release form of said memantine drug during said defined time period; and (b) said memantine drug is administered once daily in a dose range of 5 mg to 40 mg; wherein said CNS-related condition is selected from the group consisting of Alzheimer's disease and Parkinson's disease.

35. The method of claim 34, wherein said memantine drug daily dose range is 10 mg to 40 mg.

36. The method of claim 34, wherein said memantine drug and said donepezil drug are administered as a composition.

37. The method of claim 35, wherein said memantine drug and said donepezil drug are administered in a unit dosage form.

38. The method of claim 36, wherein said donepezil drug is administered in an immediate release form.

39. The method of claim 37, wherein said donepezil drug is administered in an immediate release form.

40. The method of claim 1, wherein the amount of said memantine or pharmaceutically acceptable salt thereof ranges between 20 to 40 mg per dose.

41. The method of claim 5, wherein the amount of said memantine or pharmaceutically acceptable salt thereof ranges between 12.5 to 40 mg per dose.

42. The method of claim 6, wherein the amount of said memantine or pharmaceutically acceptable salt thereof ranges between 10 to 40 mg per dose.

43. The method of claim 40, wherein said memantine or pharmaceutically acceptable salt thereof and said donepezil or a pharmaceutically acceptable salt thereof are administered in a unit dosage form.

44. The method of claim 42, wherein said memantine or pharmaceutically acceptable salt thereof and said donepezil or a pharmaceutically acceptable salt thereof are administered in a unit dosage form.

45. The method of claim 41, wherein said donepezil or a pharmaceutically acceptable salt thereof is administered in an immediate release form.

46. The method of claim 43, wherein said donepezil or a pharmaceutically acceptable salt thereof is administered in an immediate release form.

47. The method of claim 41, wherein said donepezil or a pharmaceutically acceptable salt thereof is administered in an immediate release form.

48. The method of claim 1, wherein the amount of said memantine or pharmaceutically acceptable salt thereof ranges between 22.5 mg to 40 mg per dose.

49. The method of claim 6, wherein the amount of said memantine or pharmaceutically acceptable salt thereof ranges between 22.5 mg to 40 mg per dose.

50. The method of claim 34, wherein the amount of said memantine or pharmaceutically acceptable salt thereof ranges between 12.5 mg to 40 mg per dose.

51. The method of claim 34, wherein the amount of said memantine or pharmaceutically acceptable salt thereof ranges between 20 mg to 40 mg per dose.

52. The method of claim 34, wherein the amount of said memantine or pharmaceutically acceptable salt thereof ranges between 22.5 mg to 40 mg per dose.

53. The method of claim 1, wherein the defined time period of 0 to Tmax of an immediate release form of memantine is the first 6 hours after administration.

54. The method of claim 6, wherein the defined time period of 0 to Tmax of an immediate release form of memantine is the first 6 hours after administration.

55. The method of claim 34, wherein the defined time period of 0 to Tmax of an immediate release form of memantine is the first 6 hours after administration.

56. The method of claim 48, wherein the defined time period of 0 to Tmax of an immediate release form of memantine is the first 6 hours after administration.

57. The method of claim 49, wherein the defined time period of 0 to Tmax of an immediate release form of memantine is the first 6 hours after administration.

58. The method of claim 52, wherein the defined time period of 0 to Tmax of an immediate release form of memantine is the first 6 hours after administration.

* * * * *